(12) United States Patent
Nishikawa et al.

(10) Patent No.: US 7,807,176 B2
(45) Date of Patent: Oct. 5, 2010

(54) POLYPEPTIDE PROMOTING VASCULAR ENDOTHELIAL CELL GROWTH

(75) Inventors: Tomoyuki Nishikawa, Minoo (JP); Hironori Nakagami, Ibaraki (JP); Yasufumi Kaneda, Minoo (JP)

(73) Assignee: Genomidea, Inc., Osaka (JP)

( * ) Notice: Subject to any disclaimer, the term of this patent is extended or adjusted under 35 U.S.C. 154(b) by 321 days.

(21) Appl. No.: 10/593,518

(22) PCT Filed: Mar. 17, 2005

(86) PCT No.: PCT/JP2005/004832
§ 371 (c)(1),
(2), (4) Date: May 22, 2007

(87) PCT Pub. No.: WO2005/090564
PCT Pub. Date: Sep. 29, 2005

(65) Prior Publication Data
US 2007/0281888 A1    Dec. 6, 2007

(30) Foreign Application Priority Data
Mar. 19, 2004   (JP) .............................. 2004-081688

(51) Int. Cl.
*A61K 39/00*   (2006.01)
*C07H 21/04*   (2006.01)
(52) U.S. Cl. .................................. 424/198.1; 530/324
(58) Field of Classification Search ........................ None
See application file for complete search history.

(56) References Cited

U.S. PATENT DOCUMENTS 6,479,654 B1 * 11/2002 Baird et al. ................. 536/23.5
2002/0137081 A1 * 9/2002 Bandman ....................... 435/6

FOREIGN PATENT DOCUMENTS

WO     WO /94/01548   *  1/1994
WO     WO 01/51628 A2    7/2001

OTHER PUBLICATIONS

Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Bork et al. Go hunting in sequence databases but watch out for the traps. Trends in Genetics. 12(10): 425-427, 1996.*
Smith et al. The challenges of genome sequence annotation or "The devil is in the details". Nature Biotech 15: 1222-1223, 1997.*
Doerks et al. Protein annotation: detective work for function prediction. Trends in Genetics 14(6): 248-250, 1998.*
Brenner, S.E. Errors in genome function. Trends in Genetics 15(4): 132-133, 1999.*
Bork, A. Powers and pitfalls in sequence analysis: the 70% hurdle. Genome Res 10: 398-400, 2000.*
Skolnick et al. From genes to protein structure and function: novel applications of computational approaches in the genomic era. Trends in Biotech 18(1): 34-39, 2000.*
Nakao et al., Identification of a Gen eCoding for a New Squamous Cell Carcinoma Antigen Recognized by the CTL. J Immunol. 164, 2565-2574, 2000.*

* cited by examiner

*Primary Examiner*—Lorraine Spector
*Assistant Examiner*—Elly-Gerald Stoica
(74) *Attorney, Agent, or Firm*—Mintz Levin Cohn Ferris Glovsky and Popeo, PC; Ingrid A. Beattie

(57) ABSTRACT

It is intended to provide a novel polypeptide having an activity of growing vascular endothelial cells, an activity of promoting transcription form c-fos promoter, an activity of promoting transciption from VEGF promoter and/or an angiogenic activity; a polynucleotide encoding this polypeptide; the above polypeptide and/or a pharmaceutical composition containing the polypeptide for treating a disease selected from the group consisting of obstructive arteriosclerosis, Buerger's disease, peripheral vascular disorder, angina, myocardial infraction, brain infarction, ischemic heart disease and ischemic brain disease; a method of treating these diseases; and an antibacterial composition. The above problems can be solved by isolating a novel peptide having the above-described activities and a nucleotide encoding this peptide.

9 Claims, 16 Drawing Sheets

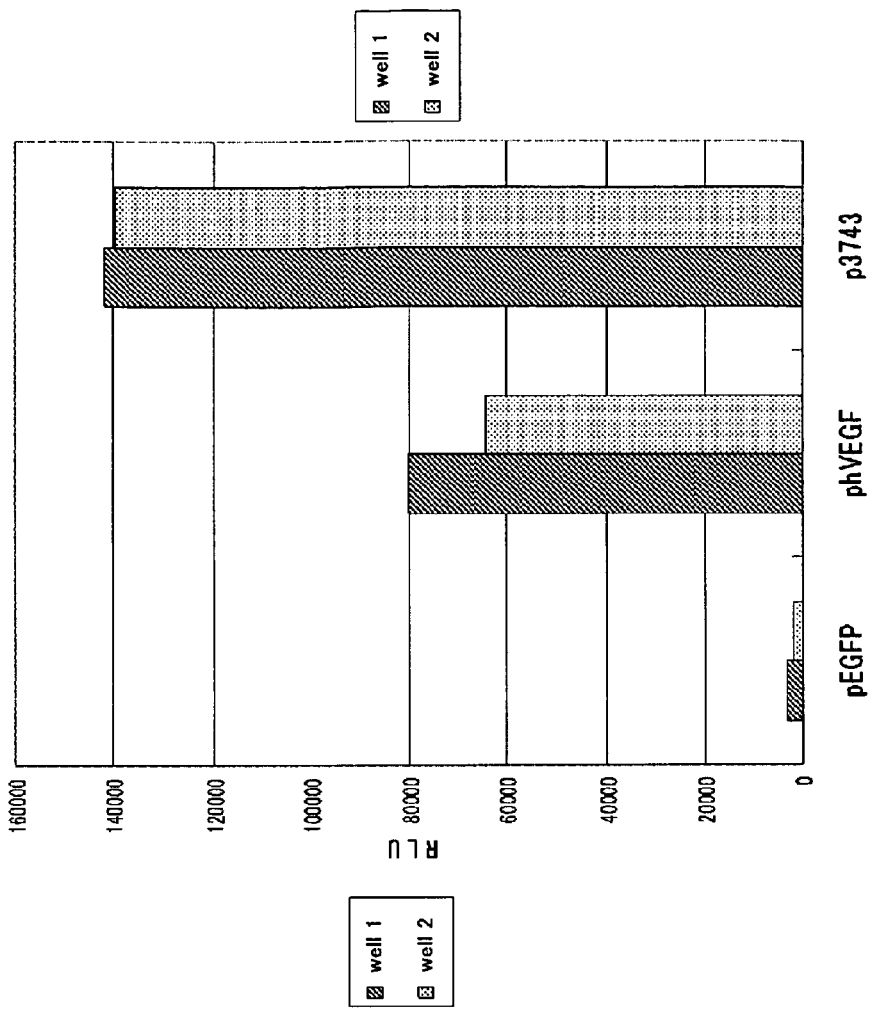
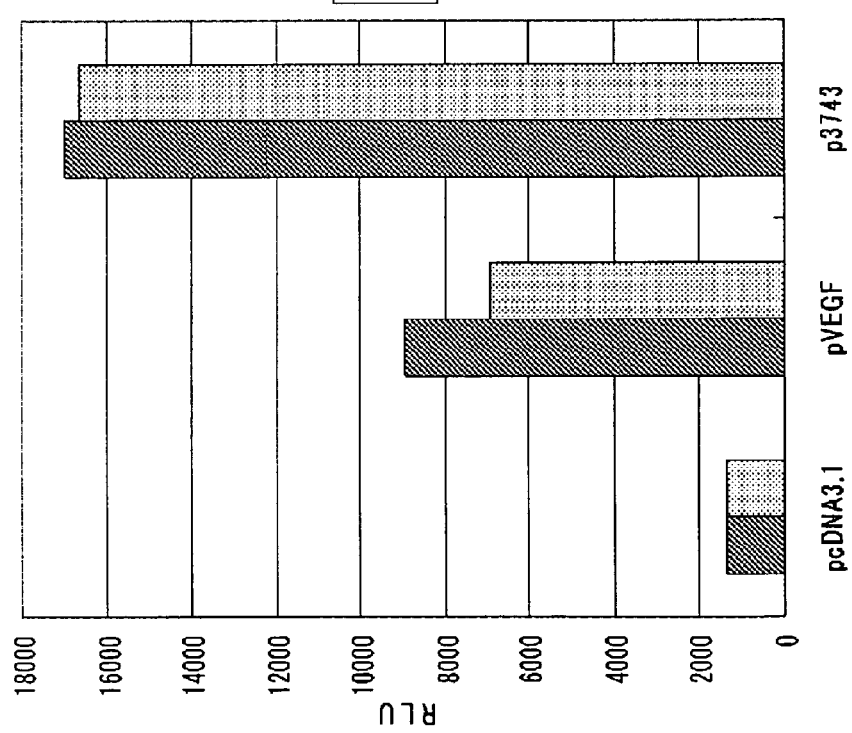
Fig. 3

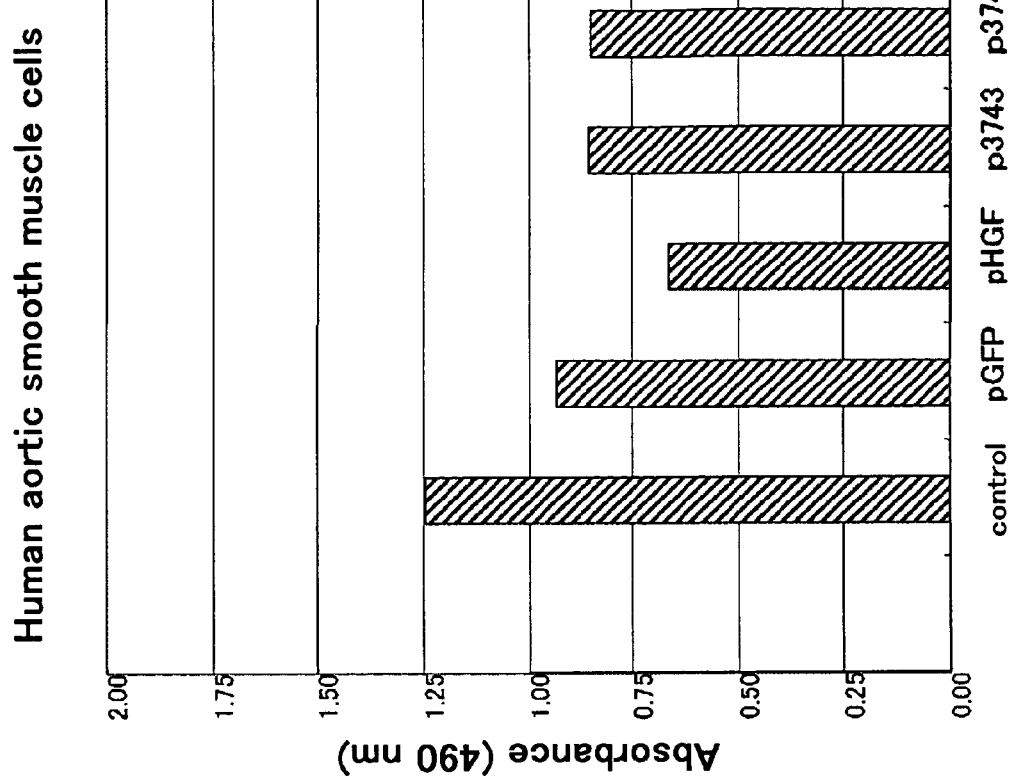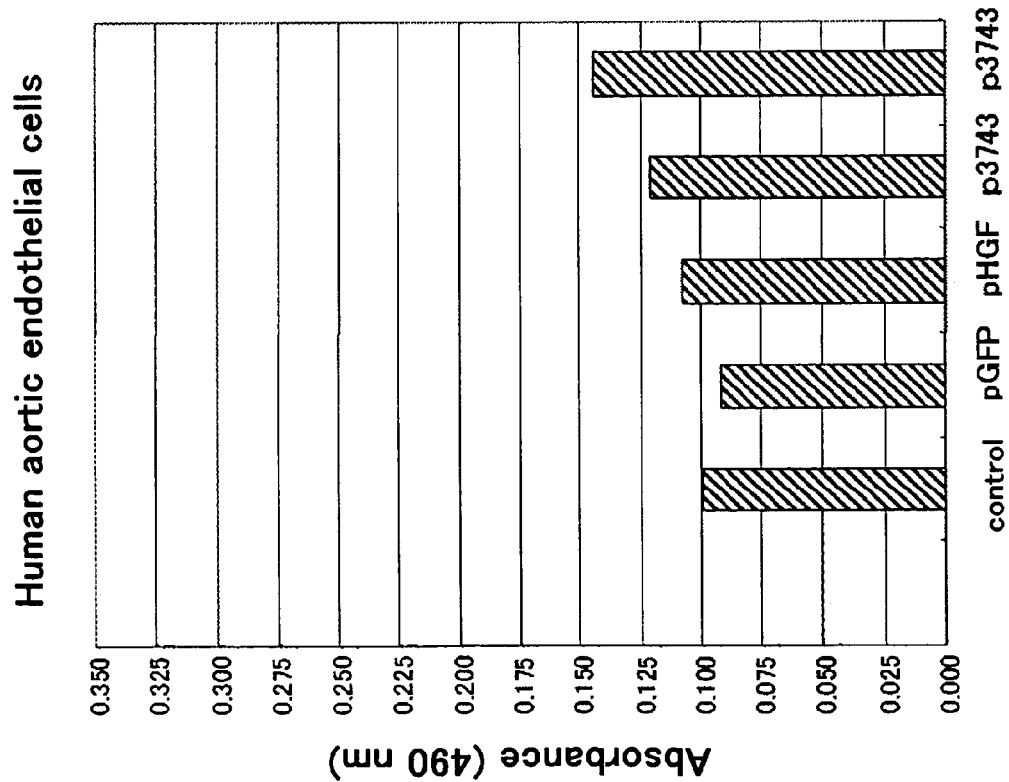
Fig. 4

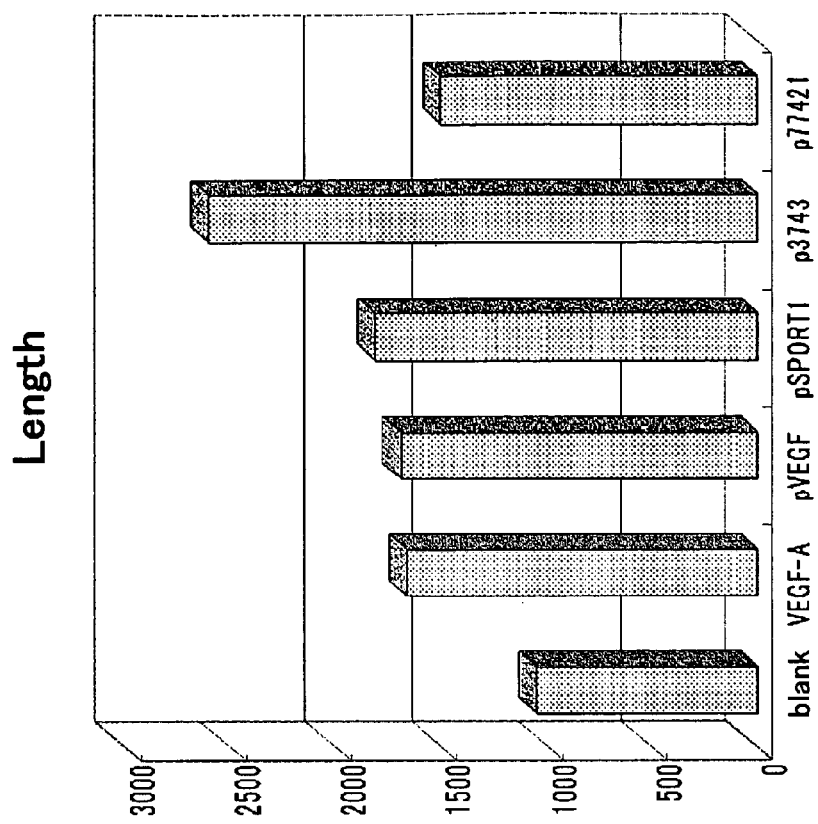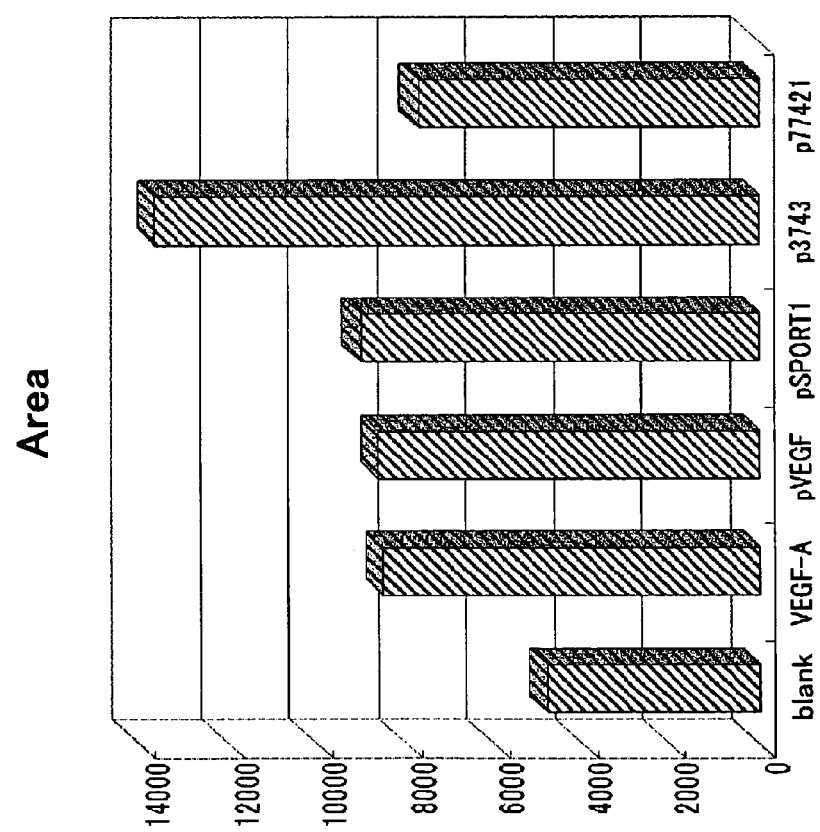
Fig. 6

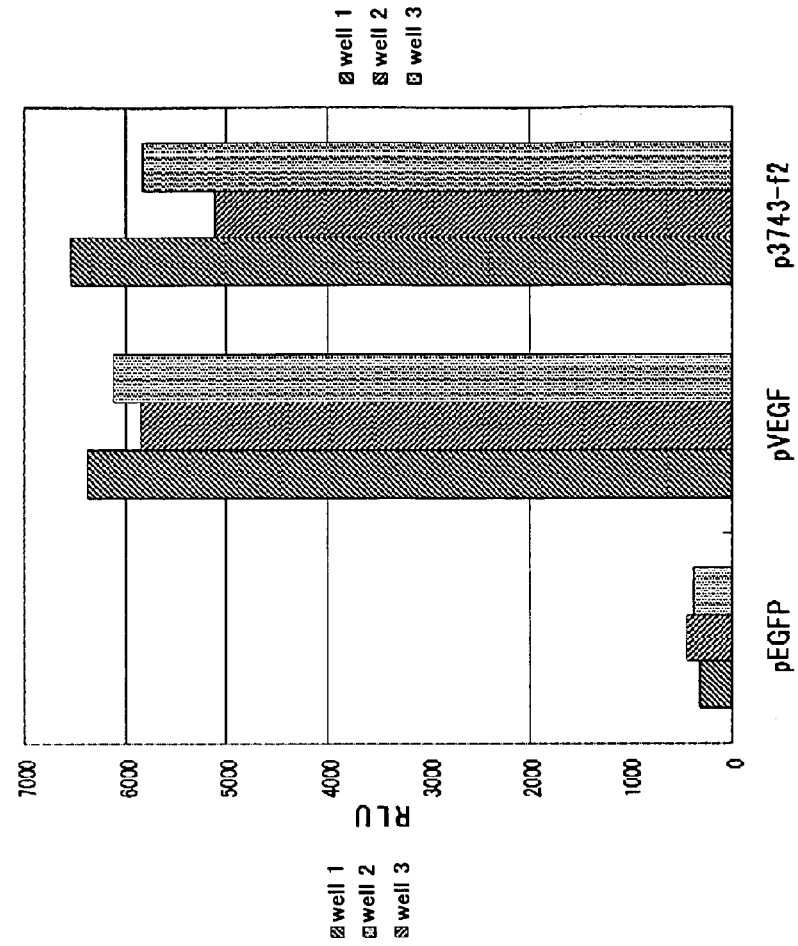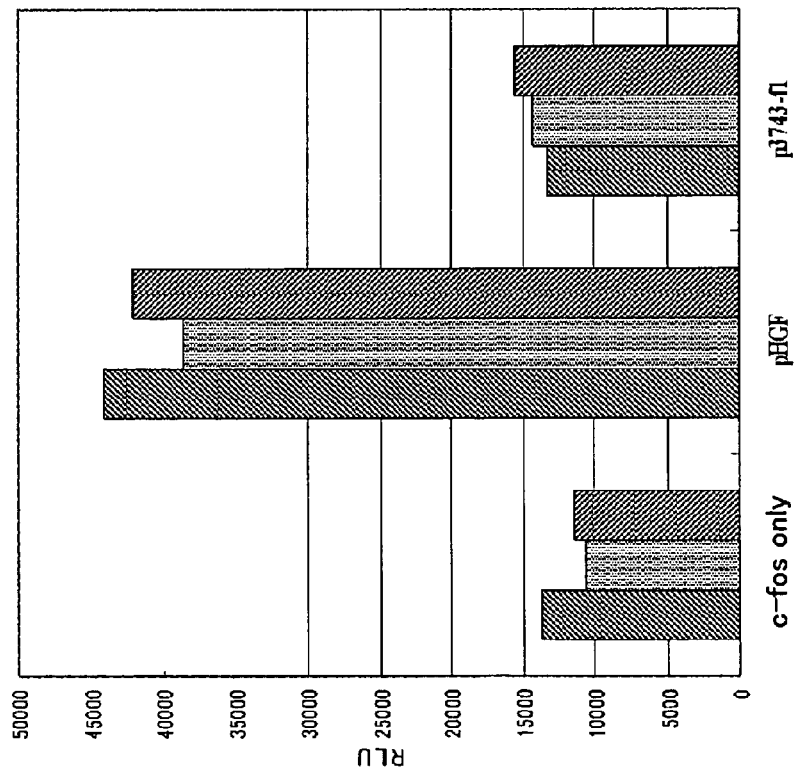
Fig. 8

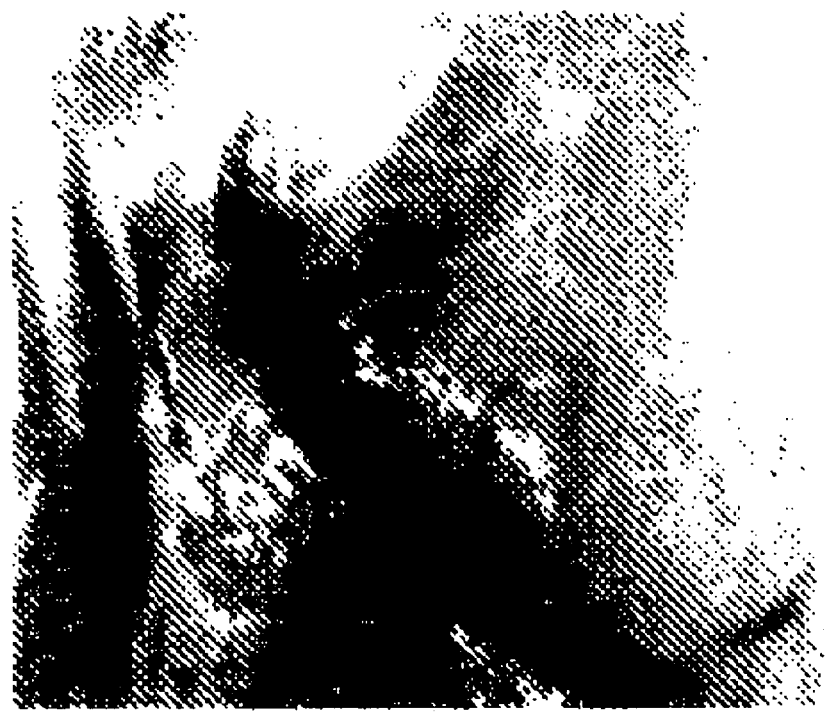
control peptide
F2 peptide
Fig. 12

Fig. 13
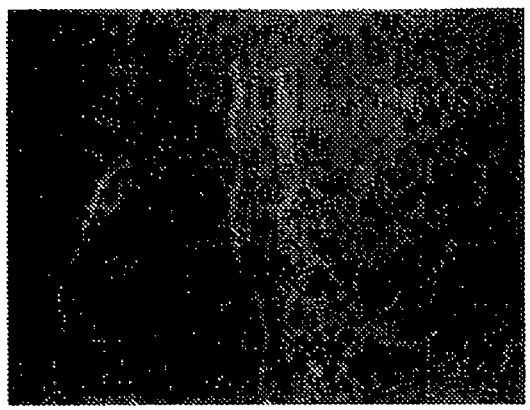
negative control
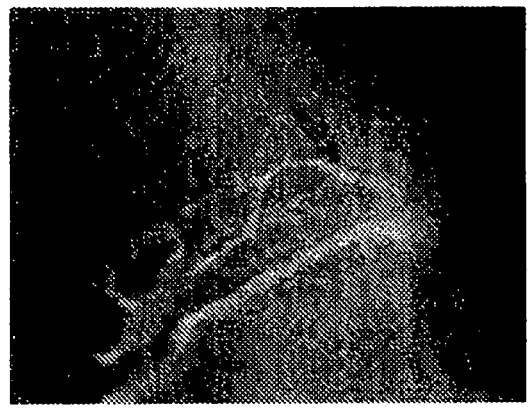
control peptide
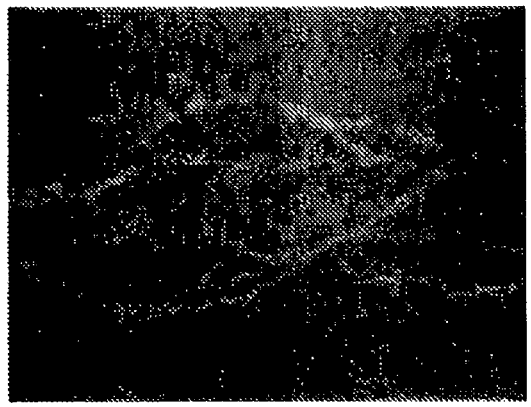
VEGF
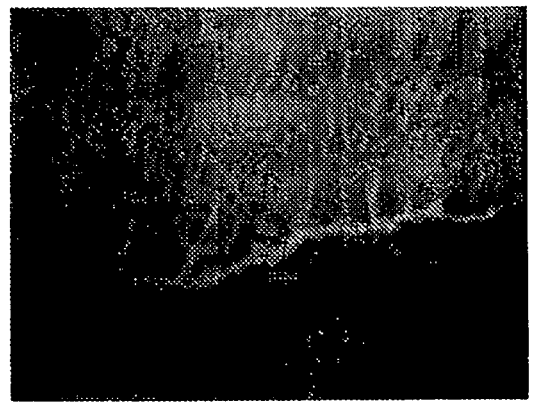
F2 peptide

```
                        SEQUENCE LISTING

<160> NUMBER OF SEQ ID NOS: 6

<210> SEQ ID NO 1
<211> LENGTH: 93
<212> TYPE: DNA
<213> ORGANISM: Homo sapiens
<220> FEATURE:
<221> NAME/KEY: CDS
<222> LOCATION: (1)..(93)

<400> SEQUENCE: 1 atg ctg tcc ctg ata ttt ttg cac aga ttg aag tca atg aga aaa aga    48
Met Leu Ser Leu Ile Phe Leu His Arg Leu Lys Ser Met Arg Lys Arg
1               5                   10                  15 tta gac aga aag ctc aga ttt tgg cac aga aag aac tac cca tag        93
Leu Asp Arg Lys Leu Arg Phe Trp His Arg Lys Asn Tyr Pro
            20                  25                  30

<210> SEQ ID NO 2
<211> LENGTH: 30
<212> TYPE: PRT
<213> ORGANISM: Homo sapiens

<400> SEQUENCE: 2

Met Leu Ser Leu Ile Phe Leu His Arg Leu Lys Ser Met Arg Lys Arg
1               5                   10                  15

Leu Asp Arg Lys Leu Arg Phe Trp His Arg Lys Asn Tyr Pro
            20                  25                  30

<210> SEQ ID NO 3
<211> LENGTH: 1663
<212> TYPE: DNA
<213> ORGANISM: Homo sapiens

<400> SEQUENCE: 3
gctgctattg tggaacagaa cttgcagcat tttaaaccag tgtttcagct gctggagaag     60
cagatactgt cccgagtccg gaacacagct agctttagga agactgctga acgcctgctg    120
agattttcag ataagagaca gactgaggag gccattgaca ggattttttgc catatcacag   180 caacagcagc agcaaagcaa gtcaaagaaa aaccgaaggg caggcaaacg ctataaattt    240
```

-continued

| | |
|---|---|
| gtggatgctg tccctgatat ttttgcacag attgaagtca atgagaaaaa gattagacag | 300 |
| aaagctcaga ttttggcaca gaaagaacta cccatagatg aagatgaaga aatgaaagac | 360 |
| cttttagatt ttgcagatgt aacatacgag aaacataaaa atgggggctt gattaaaggc | 420 |
| cggtttggac aggcacggat ggtgacaact acacacagca gggccccatc actgtctgct | 480 |
| tcctatacca ggttgttcct gattctgaac attgctattt tctttgtcat gttggcaatg | 540 |
| caactgactt atttccagag ggcccagagc ctacatggcc aaagatgtct ttatgcagtt | 600 |
| cttctcatag atagctgtat tttattatgg ttgtactctt cttgttccca atcacagtgt | 660 |
| tagcactgaa gctataaatt acctggtcat ttgtgatcaa caagagtcta tgcaaaaaaa | 720 |
| aaaatttctt taccccagat tatcagattt ttttccctca gattcatttt aacaaattaa | 780 |
| gggaagatat tttgacacaa gaaagcagga acgtggagaa attggagcag aaaagaaat | 840 |
| tatcaaagca atagaaatag cttggtggtc ctatggtgtt tttggaagta tttggcattg | 900 |
| ctaattgagc agtccatata gtactacttt tagaagaaac aaaaagtctg tttttttaaag | 960 |
| taatgttttt tcttatgaga aaaggtttta gatagaattg ggttttatta atattaattt | 1020 |
| aatgctatta gcaatttcca tatactatat tgtggaaaag actgaagaat acaattctga | 1080 |
| gaaatataaa aaaattttaa tggtatactc atgttgaaag ataaatgttg ctaagtcctg | 1140 |
| gtatgatggt gtgagcttcc ttggggaagt acttcttgag ttatgtaact aacaggatgt | 1200 |
| tttactacag atctggatgg ctattcagat aacatggcaa aaaatgatag cagaagatca | 1260 |
| ttaaaaactt aaaatatatt ttattagaaa acatttatct atgaatgaat atttccttga | 1320 |
| tgctggtctc tgcacacata tgcttggtta cttgcatgca ttcattggtt gttcaataag | 1380 |
| tgagatgatt acagataact taatactgta ttttccttat atggaaaacc gttatagacc | 1440 |
| caataacaac taaaccttc aaagaaaat atttctatt atgaatgttg attttcatac | 1500 |
| caaagaagat ggagagtcta aaatttggat atgattctta tgttttttta atagaaaacc | 1560 |
| ttcttcaagt ttattttcct aaataaacat cataattgtg aatttaaaaa aaaaaaaaaa | 1620 |
| aaaaaaaaaa aaaaaaaaaa aaaaagaaaa aaaaaaaaaa aaa | 1663 |

```
<210> SEQ ID NO 4
<211> LENGTH: 312
<212> TYPE: DNA
<213> ORGANISM: Homo sapiens
<220> FEATURE:
<221> NAME/KEY: CDS
<222> LOCATION: (1)..(312)

<400> SEQUENCE: 4
```

| | |
|---|---|
| atg aaa gac ctt tta gat ttt gca gat gta aca tac gag aaa cat aaa<br>Met Lys Asp Leu Leu Asp Phe Ala Asp Val Thr Tyr Glu Lys His Lys<br>1               5                  10               15 | 48 |
| aat ggg ggc ttg att aaa ggc cgg ttt gga cag gca cgg atg gtg aca<br>Asn Gly Gly Leu Ile Lys Gly Arg Phe Gly Gln Ala Arg Met Val Thr<br>              20                  25                 30 | 96 |
| act aca cac agc agg gcc cca tca ctg tct gct tcc tat acc agg ttg<br>Thr Thr His Ser Arg Ala Pro Ser Leu Ser Ala Ser Tyr Thr Arg Leu<br>35                      40                  45 | 144 |
| ttc ctg att ctg aac att gct att ttc ttt gtc atg ttg gca atg caa<br>Phe Leu Ile Leu Asn Ile Ala Ile Phe Phe Val Met Leu Ala Met Gln<br>              50                  55                 60 | 192 |
| ctg act tat ttc cag agg gcc cag agc cta cat ggc caa aga tgt ctt<br>Leu Thr Tyr Phe Gln Arg Ala Gln Ser Leu His Gly Gln Arg Cys Leu<br>65                      70                  75                 80 | 240 |

```
tat gca gtt ctt ctc ata gat agc tgt att tta tta tgg ttg tac tct    288
Tyr Ala Val Leu Leu Ile Asp Ser Cys Ile Leu Leu Trp Leu Tyr Ser
                85                  90                  95 tct tgt tcc caa tca cag tgt tag                                    312
Ser Cys Ser Gln Ser Gln Cys
            100

<210> SEQ ID NO 5
<211> LENGTH: 103
<212> TYPE: PRT
<213> ORGANISM: Homo sapiens

<400> SEQUENCE: 5

Met Lys Asp Leu Leu Asp Phe Ala Asp Val Thr Tyr Glu Lys His Lys
1               5                   10                  15

Asn Gly Gly Leu Ile Lys Gly Arg Phe Gly Gln Ala Arg Met Val Thr
                20                  25                  30

Thr Thr His Ser Arg Ala Pro Ser Leu Ser Ala Ser Tyr Thr Arg Leu
            35                  40                  45

Phe Leu Ile Leu Asn Ile Ala Ile Phe Phe Val Met Leu Ala Met Gln
        50                  55                  60

Leu Thr Tyr Phe Gln Arg Ala Gln Ser Leu His Gly Gln Arg Cys Leu
65                  70                  75                  80

Tyr Ala Val Leu Leu Ile Asp Ser Cys Ile Leu Leu Trp Leu Tyr Ser
                85                  90                  95

Ser Cys Ser Gln Ser Gln Cys
            100

<210> SEQ ID NO 6
<211> LENGTH: 30
<212> TYPE: PRT
<213> ORGANISM: ARTIFICIAL
<220> FEATURE:
<223> OTHER INFORMATION: CONTROL PEPTIDE

<400> SEQUENCE: 6

Arg Ser Leu Glu Gly Thr Asp Arg Phe Pro Phe Val Arg Leu Lys Asn
1               5                   10                  15

Ser Arg Lys Leu Glu Phe Lys Asp Ile Lys Gly Ile Lys Arg
                20                  25                  30
```

POLYPEPTIDE PROMOTING VASCULAR ENDOTHELIAL CELL GROWTH

TECHNICAL FIELD

The present invention relates to a novel polypeptide having vascular endothelial cell growth activity, activity in promoting transcription from c-fos promoter, activity in promoting transcription from VEGF promoter and/or an angiogenesis activity, as well as a polynucleotide encoding the polypeptide.

BACKGROUND ART

By promoting angiogenesis, it is possible to treat occlusive arterial diseases, arteriosclerosis obliterans and Buerger disease, as well as ischemic heart diseases and cerebral diseases such as angina, myocardial infarction and cerebral infarction (Non-patent documents 1 to 7).

It is estimated that dangerous ischemia of extremities occurs annually in 500 to 1000 persons per million. The majority of these patients cannot be treated by a surgery or transdermal revascularization because arterial occlusion spreads over a broad site. Accordingly, new therapies, such as angiogenesis are expected to become important in treating such patients. A number of proteins are known to promote angiogenesis, including HGF (hepatocyte growth factor) and VEGF (vascular endothelial growth factor) (Patent document 1 and 2). However, VEGF is disadvantageous in that it easily generates edema. A method of introducing a gene for increasing the level of endogenous VEGF in patients with dangerous ischemia of extremities or myocardial ischemia has been studied. However, VEGF therapy for these patients may cause limb edema as a side-effect of the therapy. Blood-brain barrier leakage in the ischemic brain due to VEGF is also reported. HGF increases the ability of cells to migrate upon administration thereof, but is disadvantageous in that where cancer occurs, there is a risk of inducing the metastasis of the cancer. Accordingly, there is need for a novel polypeptide for the treatment of occlusive arterial diseases, arteriosclerosis obliterans and Buerger disease, as well as ischemic heart diseases and cerebral diseases such as angina, myocardial infarction and cerebral infarction.

Patent document 1: Japanese National Phase PCT Laid-Open Publication No. 10-51071
Patent document 2: Japanese National Phase PCT Laid-Open Publication No. 2001-517075
Non-patent document 1: KEKKAN SHINSEI RYOHO-KISO TO RINSYO—(Angiogenesis Therapy—Fundamental and Clinical-), edited by Yasumi Uchida & Yutaka Kozuka, Medical Book Publication Department in Shinko Trading Co., Ltd., May 25, 1997;
Non-patent document 2: The FASEB J. 17 779-781, 2003
Non-patent document 3: Circulation 97, 1114-1123, 1998
Non-patent document 4: The Lancet, 348, 370-374, 1996
Non-patent document 5: Circulation 105, 1491-96, 2002
Non-patent document 6: Gene Therapy 7, 417-427, 2000
Non-patent document 7: Circulation 109, 424-431, 2004

DISCLOSURE OF THE INVENTION

Problem to be Solved by the Present Invention

An object of the present invention is to provide a novel polypeptide having vascular endothelial cell growth activity, activity in promoting transcription from c-fos promoter, activity in promoting transcription from VEGF promoter and/or angiogenesis activity, as well as a polynucleotide encoding the polypeptide. Furthermore, the object of the present invention is to provide a pharmaceutical composition for the treatment of a disease selected from the group consisting of arteriosclerosis obliterans, Buerger disease, peripheral blood vessel disease, angina, myocardial infarction, cerebral infarction, ischemic heart disease, and ischemic cerebral disease, which comprises the polypeptide and/or the polypeptide, as well as a method of treating these diseases.

Means to Solve the Problems

On the basis of a finding that it is highly possible for vascular endothelial growth-promoting factor to promote angiogenesis, the present invention was completed by isolating a nucleic acid encoding a novel peptide using a novel screening method.

The present invention provides as follows:
1. A polynucleotide selected from the group consisting of:
   (a) a polynucleotide containing a nucleotide sequence set forth in SEQ ID NO:1 or a fragment thereof;
   (b) a polynucleotide containing a sequence encoding an amino acid sequence set forth in SEQ ID NO:2 or a fragment thereof;
   (c) a polynucleotide encoding a variant polypeptide wherein in a amino acid sequence set forth in SEQ ID NO:2, one or more amino acids thereof have at least one mutation selected from the group consisting of substitution, addition and deletion;
   (d) a polynucleotide hybridizing under stringent conditions with any of the polynucleotides (a) to (c); and
   (e) a polynucleotide consisting of a nucleotide sequence having at least 70% identity with any of the polynucleotides (a) to (c) or sequences complementary thereto,
   wherein the polynucleotide encodes a peptide having an activity selected from the group consisting of vascular endothelial cell growth activity, activity in promoting transcription from c-fos promoter, activity in promoting transcription from VEGF promoter, and angiogenesis activity.
2. The polynucleotide according to claim 1, which has a nucleotide sequence set forth in SEQ ID NO:1.
3. The polynucleotide according to claim 1, which encodes an amino acid sequence set forth in SEQ ID NO:2.
4. The polynucleotide according to claim 1, which encodes a peptide having angiogenesis activity.
5. The polynucleotide according to claim 1, which encodes a peptide having vascular endothelial cell growth activity.
6. A pharmaceutical composition for angiogenesis, which comprises the polynucleotide of claim 1.
7. A pharmaceutical composition for growth of vascular endothelial cells, which comprises the polynucleotide of claim 1.
8. A pharmaceutical composition for treatment of a disease selected from the group consisting of occlusive arterial disease, arteriosclerosis obliterans, Buerger disease, angina, myocardial infarction, cerebral infarction, ischemic heart disease, and ischemic cerebral disease, which comprises the polynucleotide of claim 1.
9. A method of generating angiogenesis of tissue, comprising:
   (1) a step of providing tissue for angiogenesis; and
   (2) a step of introducing a nucleic acid containing the polynucleotide of claim 1 into a vascular endothelial cell.
10. The method according to claim 9, wherein the angiogenesis is carried out in vivo, ex vivo or in vitro.
11. The method according to claim 9, wherein the tissue is in a disease-state selected from the group consisting of occlusive arterial disease, arteriosclerosis obliterans, Buerger disease, angina, myocardial infarction, cerebral infarction, ischemic heart disease, and ischemic cerebral disease.

12. A method of proliferating a vascular endothelial cell, comprising:
   (1) a step of providing a vascular endothelial cell; and
   (2) a step of introducing a nucleic acid containing the polynucleotide of claim 1 into the vascular endothelial cell.
13. The method according to claim 12, wherein the proliferation of the vascular endothelial cell is carried out in vivo, ex vivo or in vitro.
14. The method according to claim 12, wherein the vascular endothelial cell is in tissue affected by a disease selected from the group consisting of occlusive arterial disease, arteriosclerosis obliterans, Buerger disease, angina, myocardial infarction, cerebral infarction, ischemic heart disease, and ischemic cerebral disease.
15. A plasmid comprising the polynucleotide of claim 1.
16. A gene-transfer vector comprising the polynucleotide of claim 1.
17. A method of proliferating a vascular endothelial cell, comprising:
   (1) a step of providing a vascular endothelial cell; and
   (2) a step of contacting the gene-transfer vector of claim 16 with the vascular endothelial cell.
18. A polypeptide encoded by the polynucleotide of claim 1.
19. A polypeptide selected from the group consisting of:
   (a) a polypeptide containing an amino acid sequence encoded by a nucleotide sequence set forth in SEQ ID NO:1 or a fragment thereof;
   (b) a polypeptide containing an amino acid sequence set forth in SEQ ID NO:2 or a fragment thereof;
   (c) a variant polypeptide wherein in an amino acid sequence set forth in SEQ ID NO:2, one or more amino acids have at least one mutation selected from the group consisting of substitution, addition and deletion; and
   (d) a polypeptide consisting of an amino acid sequence having at least 70% identity with an amino acid sequence of any one of the polypeptides (a) to (c),
   wherein the polypeptide has an activity selected from the group consisting of a vascular endothelial cell growth activity, activity in promoting transcription from c-fos promoter, activity in promoting transcription from VEGF promoter, and angiogenesis activity.
20. The polypeptide according to claim 19, which is encoded by a nucleotide sequence set forth in SEQ ID NO:1.
21. The polypeptide according to claim 19, which has an amino acid sequence set forth in SEQ ID NO:2.
22. The polypeptide according to claim 19, which has angiogenesis activity.
23. The polypeptide according to claim 19, which has vascular endothelial cell growth activity.
24. A pharmaceutical composition for angiogenesis, which comprises the polypeptide of claim 19.
25. A pharmaceutical composition for growth of vascular endothelial cells, which comprises the polypeptide of claim 19.
26. A pharmaceutical composition for the treatment of a disease selected from the group consisting of occlusive arterial disease, arteriosclerosis obliterans, Buerger disease, angina, myocardial infarction, cerebral infarction, ischemic heart disease, and ischemic cerebral disease, which comprises the polypeptide of claim 19.
27. A method of generating angiogenesis of tissue, comprising:
   (1) a step of providing tissue for angiogenesis; and
   (2) a step of contacting the polypeptide of claim 19 with a vascular endothelial cell.
28. The method according to claim 27, wherein the angiogenesis is carried out in vivo, ex vivo or in vitro.
29. The method according to claim 27, wherein the tissue is in a disease state selected from the group consisting of occlusive arterial disease, arteriosclerosis obliterans, Buerger disease, angina, myocardial infarction, cerebral infarction, ischemic heart disease, and ischemic cerebral disease.
30. A method of proliferating a vascular endothelial cell, comprising:
   (1) a step of providing a vascular endothelial cell; and
   (2) a step of contacting the polypeptide of claim 18 with the vascular endothelial cell.
31. The method according to claim 30, wherein the proliferation of the vascular endothelial cell is carried out in vivo, ex vivo or in vitro.
32. The method according to claim 30, wherein the vascular endothelial cell is in tissue affected by a disease selected from the group consisting of occlusive arterial disease, arteriosclerosis obliterans, Buerger disease, angina, myocardial infarction, cerebral infarction, ischemic heart disease, and ischemic cerebral disease.
33. An antimicrobial agent comprising the polynucleotide of claim 1.
34. An antimicrobial agent comprising the polypeptide of claim 18 or 19.
35. A pharmaceutical composition for treating infections, which comprises the polynucleotide of claim 1.
36. A pharmaceutical composition for treating infections, which comprises the polypeptide of claim 18 or 19.
37. A composition for enhancing the production of IGF, which comprises the polynucleotide of claim 1.
38. A composition for enhancing the production of IGF, which comprises the polypeptide of claim 18 or 19.

Effects of the Present Invention

According to the present invention, there is provided a polypeptide having at least one activity selected from vascular endothelial cell growth activity, activity in promoting transcription from c-fos promoter, activity in promoting transcription from VEGF promoter and angiogenesis activity, as well as a polynucleotide encoding the polypeptide.

According to the present invention, there is also provided a method for treatment of a disease selected from the group consisting of arteriosclerosis obliterans, Buerger disease, peripheral blood vessel disease, angina, myocardial infarction, cerebral infarction, ischemic heart disease, and ischemic cerebral disease, as well as a pharmaceutical composition for the treatment of these diseases.

BRIEF DESCRIPTION OF DRAWINGS

FIG. 3 shows the results of a c-fos promoter assay and VEGF promoter assay for clone p3743 isolated in the present invention.

FIG. 4 shows the results of an MTS assay in human aortic endothelial cells and human aortic smooth muscle cells.

FIG. 6 is a graph showing image analysis by angiogenesis quantification software.

FIG. 7 is a graph schematically showing the candidate sequences of the present invention.

FIG. 8 shows the results of a c-fos promoter assay for p3743-f1 and p3743-f2.

FIG. 12 shows the results of the in vivo angiogenesis promotion activity of F2 peptide. The result of a control peptide as a comparative control are also shown.

FIG. 13 shows the results of the in vivo angiogenesis promotion activity of F2 peptide using immune staining with anti-CD31 antibody. The results of a negative control, a control peptide and VEGF as comparative controls are also shown.

DESCRIPTION OF SEQUENCE LISTING

Figure 1:
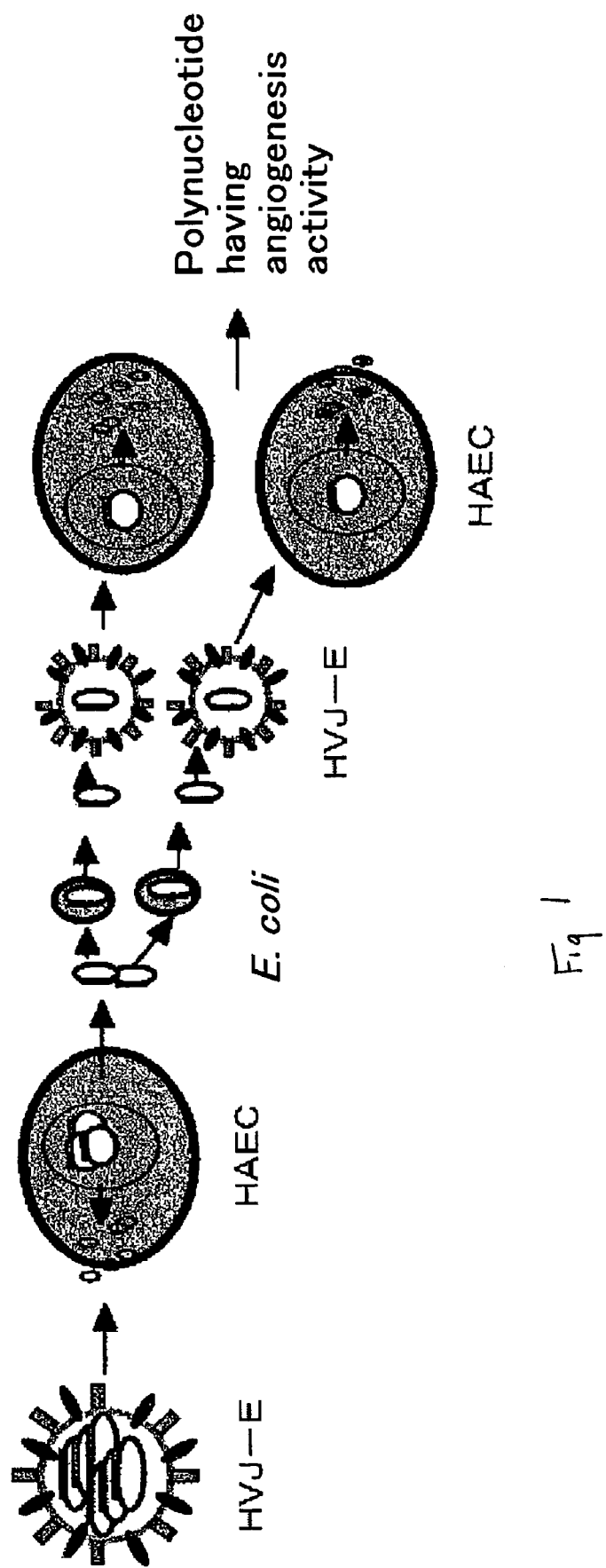
FIG. 1 is a scheme for the isolation of the nucleic acid of the present invention.

SEQ ID NO: 1 is a nucleic acid sequence encoding novel peptide F2 having angiogenesis activity.

SEQ ID NO: 2 is an amino acid sequence of novel peptide F2 having angiogenesis activity.

SEQ ID NO: 3 is an insert sequence in plasmid p3743.

SEQ ID NO: 4 is a nucleic acid sequence encoding novel peptide F1 having angiogenesis activity.

SEQ ID NO: 5 is an amino acid sequence of novel peptide F1 having angiogenesis activity.

SEQ ID NO: 6 is a control peptide for measurement of the migration activity of endothelial cells.

BEST MODE FOR CARRYING OUT THE INVENTION

Hereinafter, the present invention is described. Unless otherwise noted, it should be appreciated that expression of a singular form throughout this specification also encompasses its plural form. Unless otherwise noted, it should therefore be construed that the article or adjective (for example, "a", "an", "the", and the like) of a singular form also encompasses the concept of its plural form. Unless otherwise specified, it should be appreciated that any terms used in this specification are used in usual meaning used in the art. Accordingly, unless otherwise specified all technical terms and scientific terms used in this specification have the same meanings as generally understood by those skilled in the art to which the present invention belongs. If there is a conflict therebetween, this specification (including definitions) rules.

DEFINITIONS OF THE TERMS

Hereinafter, definitions of the terms used in this specification are listed.

As used herein, "homology" amongst genes (for example, nucleic acid sequences, amino acid sequences and the like) refers to the degree of identity between two or more gene sequences. As used herein, the identity between sequences (nucleic acid sequences, amino acid sequences and the like) refers to the degree to which each sequence amongst two or more sequences, can be compared to one another. Therefore, as the homology of two genes increases, the identity or similarity of their sequences is increased. Whether two genes have homology or not can be examined by direct comparison of their sequences or, when the sequences are nucleotide sequences, by a hybridization method under stringent conditions. When sequences of two genes are directly compared, the genes have homology when the DNA sequences of the genes are identical, typically by at least 50%, preferably at least 70%, more preferably at least 80%, 90%, 95%, 96%, 97%, 98% or 99% among gene sequences. In this specification, the "similarity" amongst genes (for example, nucleic acid sequences, amino acid sequences and the like) refers to the degree of identity between two or more gene sequences, assuming that conservative substitutions are positive (the same) in the above homology. Therefore, when conservative substitutions are present, homology and similarity are different from each other, depending on the presence of conservative substitutions. When there is no conservative substitution, the homology and similarity are indicated by the same numerical value.

As used herein, amino acid sequences or nucleotide sequences can be compared for similarity, identity and homology by calculation with the sequence analysis tool FASTA, with default parameters.

In this specification, a "fragment" refers to a polypeptide or polynucleotide having a sequence length of from 1 to n−1 relative to a full-length polypeptide or polynucleotide (whose length is n). The length of a fragment can be changed depending on the object, and the lower limit of a polypeptide for example is a length of 3, 4, 5, 6, 7, 8, 9, 10, 15, 20, 25, 30, 40, 50 or more amino acids, and a length expressed by an integer not specifically enumerated herein (for example, 11 or the like) can also be suitable as the lower limit. The lower limit of a polynucleotide is a length of 5, 6, 7, 8, 9, 10, 15, 20, 25, 30, 40, 50, 75, 100 or more nucleotides, and a length expressed by an integer not specifically enumerated herein (for example, 11 or the like) can also be suitable as the lower limit. In this specification, the length of a polypeptide or polynucleotide can be expressed as the number of amino acids or nucleotides as described above. The above-mentioned numbers are not absolute, and it is intended that as long as the same function is maintained, the above-mentioned numbers as the upper or lower limits include greater or smaller number by several amino acids or nucleotides or by ±10%, for example. With this intention, the term "about" is prefixed sometimes to the number of amino acids or nucleotides in this specification. As used herein, however, it should be appreciated that the interpretation of the numerical value is not influenced regardless of whether the term "about" is present or absent. The length of a useful fragment in this specification can be determined by examining whether or not the fragment retains at least one of functions of its standard, i.e. full-length, protein.

As used herein, an "isolated" biological factor (for example, a nucleic acid or a protein) refers to a factor substantially separated or purified from other biological factors (for example, in the case of nucleic acid, non-nucleic-acid factors and nucleic acids containing nucleic acid sequences other than the nucleic acid of interest, or in the case of protein, non-protein factors and proteins containing amino acid sequences other than the protein of interest) in cells of a living organism in which the biological factor occurs naturally. An isolated nucleic acid or protein includes a nucleic acid or protein purified by standard purification methods. Accordingly, the isolated nucleic acid or protein includes chemically synthesized nucleic acids and proteins.

As used herein, a "purified" biological factor (for example, a nucleic acid or a protein) refers to a biological factor from which at least a part of its naturally accompanying factors has been removed. Accordingly, the purified biological factor is usually of higher purity than in the usual state of the biological factor (that is, the biological factor is concentrated).

The terms "purified" and "isolated" as used herein mean that the same biological factor is present by preferably at least 75 wt %, more preferably at least 85 wt %, still more preferably at least 95 wt %, and most preferably 98 wt %.

As used herein, a "gene-transfer vector" and a "gene vector" are interchangeably used. Both t "gene-transfer vector" and "gene vector" refer to a vector capable of transferring a polynucleotide sequence of interest into a cell of interest. The terms "gene-transfer vector" and "gene vector" include, but are not limited to, "virus envelope vector" and "liposome vector".

As used herein, the "virus envelope vector" refers to a vector having an exogenous gene encapsulated in a virus envelope, or to a vector having an exogenous gene encapsulated in a component containing a virus envelope-derived protein. The virus used in the preparation of the gene-transfer vector may be a wild-type virus or a recombinant virus.

In the present invention, the virus used in preparing the virus envelope or virus envelope-derived protein includes, but is not limited to, viruses belonging to a family selected from the group consisting of the families Retroviridae, Togaviridae, Coronaviridae, Flaviviridae, Paramyxoviridae, Orthomyxoviridae, Bunyaviridae, Rhabdoviridae, Poxviridae, Herpesviridae, Baculoviridae and Hepadnaviridae. Preferably, a virus belonging to the family Paramyxoviridae, more preferably HVJ (Sendai virus), is used.

The virus envelope-derived protein includes, but is not limited to, e.g. F protein, HN protein, NP protein and M protein of HVJ.

As used herein, a "liposome vector" refers to a vector having an exogenous gene encapsulated in a liposome. Lipids used in the preparation of the liposome vector include, but are not limited to, neutral phospholipids such as DOPE (dioleoyl phosphatidyl ethanolamine) and phosphatidylcholine, negatively charged phospholipids such as cholesterol, phosphatidyl serine and phosphatidic acid, and positively charged lipids such as DC-cholesterol (dimethyl aminoethane carbamoyl cholesterol) and DOTAP (dioleoyl trimethyl ammonium propane).

As used herein, "liposome" comprises a type of lipid bilayer. For example, a closed vesicle consisting of a lipid bilayer having an aqueous phase in the inside thereof is formed by suspending a phospholipid such as lecithin at 50% or more (weight ratio) in water at a temperature not lower than the gel/liquid crystal phase transition temperature inherent to the phospholipid. This vesicle is referred to as a liposome. The vesicle is divided roughly into a multilamellar vesicle (MLV) wherein several bi-molecule membranes are layered in the form of an onion, and a uni-lamellar liposomes having one layer. The latter can also be prepared by vigorously stirring a suspension of phospholipid such as phosphatidylcholine by a mixer thereby dispersing the suspension, followed by sonication thereof.

Liposomes having one layer are further classified depending on particle diameter into small unilamellar vesicles (SUV) and large unilamellar vesicles (LUV). MLV is prepared by adding water to a lipid thin film and then mechanically vibrating such. SUV is prepared by sonication of MLV or by removal of a surfactant from a mixed solution of lipid and a surfactant, by dialysis and the like. In addition, well-known methods are (1) a method of preparing LUV by repeatedly freezing and thawing SUV, (2) a method of preparing LUV by fusing SUVs made of acidic phospholipid, in the presence of $Ca^{2+}$, and removing the $Ca^{2+}$ with EDTA (ethylenediaminetetraacetic acid), and (3) a method of preparing LUV and the like by distilling ether away from an emulsion consisting of water and a ether solution of lipid and simultaneously converting its phase (reverse-phase evaporation (REV) liposome).

As used herein, "inactivation" refers to a virus whose genome was inactivated. This inactivated virus is replication-deficient. Preferably, this inactivation is carried out by treatment with UV or an alkylating agent.

In this specification, "HVJ" and "Sendai virus" are used interchangeably. For example, the terms "HVJ envelope" and "Sendai virus envelope" are used to have the same meaning.

In this specification, "Sendai virus" refers to a virus having cell fusion action, belonging to the genus Paramyxovirus in the family Paramyxoviridae. The virus particle has a polymorphic envelope having a particle diameter of 150 to 300 nm. The genome is a minus strand RNA with a length of about 15500 bases. It has an RNA polymerase, is thermally instable, agglutinates almost all kinds of erythrocytes, and exhibits hemolysis.

In this specification, "HAU" refers to the activity of a virus capable of agglutinating 0.5% chicken erythrocytes, and 1 HAU corresponds to the activity of about 24 million virus particles (Okada, Y. et al., Biken Journal 4, 209-213, 1961).

As used herein, an "antimicrobial agent" refers to an agent having an activity which terminates, suppresses and/or delays the growth of a living organism selected from the group consisting of prokaryotes and fungi. The prokaryote to which the antimicrobial agent of the present invention is applied includes, but is not limited to, prokaryotic cells belonging to a genus selected from the group consisting of *Escherichia, Bacillus, Streptococcus, Staphylococcus, Haemophilus, Neisseria, Actinobacillus, Acinetobacter, Serratia, Brevibacterium, Corynebacterium, Microbacterium* and *Pseudomonas*. The fungal cells to which the antimicrobial agent of the present invention is applied to includes, but is not limited to, fungi belonging to a genus selected from the group consisting of yeast strains belonging to *Saccharomyces, Schizosaccharomyces, Kluyveromyces, Trichosporon, Schwanniomyces, Candida, Pichia* and the like and fungi belonging to *Neurospora*.

As used herein, "infection" is a disease in higher animals such as mammals, caused by the growth of a living organism selected from the group consisting of prokaryotes and fungi.

In this specification, "stringent conditions for hybridization" refers well-known conditions, routinely used in the art. Such polynucleotides can be obtained by a colony hybridization method, a plaque hybridization method or a Southern blot hybridization method, and the like, where a polynucleotide selected from the polynucleotides of the present invention is used as a probe. The polynucleotide refers specifically to a polynucleotide which can be identified by hybridizing a sample with a filter having immobilized colony- or plaque-derived DNA in the presence of 0.7 to 1.0 M NaCl at 65° C., and then washing the filter with SSC (saline-sodium citrate) solution at 0.1- to 2-fold concentration (SSC solution at 1-fold concentration is composed of 150 mM sodium chloride and 15 mM sodium citrate) at 65° C. Hybridization can be carried out according to methods described in laboratory books such as Molecular Cloning 2nd ed., Current Protocols in Molecular Biology, Supplement 1-38, DNA Cloning 1: Core Techniques, A Practical Approach, Second Edition, Oxford University Press (1995) and the like. Preferably, sequences containing an A or T sequence only are excluded from sequences hybridizing under stringent conditions. A "hybridizable polynucleotide" refers to a polynucleotide hybridizable with another polynucleotide under the hybridizing conditions described above. Specifically, the hybridizable polynucleotide includes polynucleotides having at least 60% or more, preferably 80% or more, and still more preferably 95% or more homology with the nucleotide sequence of DNA encoding a polypeptide having the amino acid sequence shown specifically in the present invention.

In this specification, "highly stringent conditions" refer to conditions designed so as to enable hybridization between DNA strands having a high degree of complementarity in their nucleic acid sequences, and to exclude hybridization of DNAs having significant mismatches. The stringency of hybridization is determined mainly by conditions such as temperature, ionic strength, and denaturants such as formamide. Examples of such "highly stringent conditions" regarding hybridization and washing are 0.0015 M sodium chloride, 0.0015 M sodium citrate, 65 to 68° C., or 0.015 M sodium chloride, 0.0015 M sodium citrate, and 50% formamide, 42° C. For such highly stringent conditions, see Sambrook et al., Molecular Cloning: A Laboratory Manual, 2nded., Cold Spring Harbor Laboratory (Cold Spring Harbor, N.Y. 1989); and Anderson et al., Nucleic Acid Hybridization: a Practical approach, IV, IRL Press Limited (Oxford, England). If necessary, higher stringency conditions (for example, higher temperature, lower ionic strength, higher formamide, or another denaturant) may also be used. For the purpose of reducing nonspecific hybridization and/or background hybridization, other agents can be contained in a hybridization buffer solution and a washing buffer solution. Examples of such other agents include 0.1% bovine serum albumin, 0.1% polyvinyl pyrrolidone, 0.1% sodium pyrophosphate, 0.1% sodium dodecyl sulfate (NaDodSO$_4$ or SDS), Ficoll, Denhardt's solution, sonicated salmon sperm DNA (or other uncomplimentary DNA) and dextran sulfate, but other suitable agents can also be used. The concentrations and types of these additives can be changed without having any substantial effects on the stringency of hybridization conditions. The hybridization experiment can be carried out usually at pH 6.8 to 7.4, but under a typical ionic strength condition, the rate of hybridization is almost pH-independent. See Anderson et al., Nucleic Acid Hybridization: a Practical Approach, Chapter 4, IRL Press Limited (Oxford, England).

The factor influencing the stability of a double-strand of DNA includes the base composition, length, and the degree of mismatched base pairs, thereof. Those skilled in the art can adjust hybridization conditions, can apply these variables and so enable formation of a hybrid of different sequence-related DNA. The melting temperature of a completely matched double-stranded chain of DNA can be roughly estimated according to the following equation:

$$T_m(° C.)=81.5+16.6(\log[Na^+])+0.41(\% G+C)-600/N-0.72(\% \text{formamide})$$

wherein N is the length of a double-strand formed, [Na$^+$] is the molar concentration of sodium ions in the hybridization solution or washing solution, % G+C is percentage of (guanine+cytosine) bases in a hybrid. The melting temperature of an incompletely matched hybrid is decreased by about 1° C. per 1% mismatches.

As used herein, "moderately stringent conditions" refer to conditions under which a double-strand DNA molecule having a higher degree of base pair mismatchs than that of double-strand DNA molecule formed under "highly stringent conditions" can be formed. A typical example of "moderately stringent conditions" is 0.015 M sodium chloride, 0.0015 M sodium citrate, 50 to 65° C., or 0.015 M sodium chloride, 0.0015 M sodium citrate, and 20% formamide, 37 to 50° C. For example, the "moderately stringent" conditions at 0.015 M sodium ions at 50° C. allow about 21% mismatches.

It is appreciated by those skilled in the art that in this specification, there can be cases where there is no complete discrimination between the "highly" stringent conditions and "moderately" stringent conditions. For example, the melting temperature of long-chain DNA matching completely in 0.015 M sodium ion (in the absence of formamide) is about 71° C. When washing at 65° C. (at the same ionic strength), this allows about 6% mismatches. For isolating a less related sequence, those skilled in the art can simply lower the temperature or increase the ionic strength.

A suitable rough estimate of the melting temperature of an oligonucleotide probe of up to about 20 nucleotides in 1 M NaCl is provided by Tm=(2° C. per base pair of A-T)+(4° C. per base pair of G-C). The concentration of sodium ions in 6×sodium citrate (SSC) is 1 M (see Suggs et al., Developmental Biology Using Purified Genes, p. 683, Brown and Fox (ed.) (1981)).

A natural nucleic acid encoding a protein such as a polypeptide having the amino acid sequence of SEQ ID NO: 2, a variant thereof, or a fragment thereof, can be easily isolated from a cDNA library with a hybridization probe and a PCR primer containing, for example, a part of the nucleic acid sequence of SEQ ID NO: 1 or a variant thereof. The nucleic acid encoding a polypeptide having the amino acid sequence of SEQ ID NO: 2, a variant thereof, or a fragment thereof, can hybridize with one sequence set forth in SEQ ID NO: 1 or a part thereof, under low stringency conditions defined by a hybridization buffer substantially comprising 1% bovine serum albumin (BSA), 500 mM sodium phosphate (NaPO$_4$), 1 mM EDTA, and 7% SDS at a temperature of 42° C. and a washing buffer substantially comprising 2×SSC (600 mM NaCl; 60 mM sodium citrate) and 0.1% SDS at 50° C.; more preferably under low stringency conditions defined by a hybridization buffer substantially comprising 1% bovine serum albumin (BSA), 500 mM sodium phosphate (NaPO$_4$), 15% formamide, 1 mM EDTA, and 7% SDS at a temperature of 50° C. and a washing buffer substantially comprising 1×SSC (300 mM NaCl; 30 mM sodium citrate) and 1% SDS at 50° C.; most preferably under low stringency conditions defined by a hybridization buffer substantially comprising 1% bovine serum albumin (BSA), 200 mM sodium phosphate (NaPO$_4$), 15% formamide, 1 mM EDTA, and 7% SDS at a temperature of 50° C. and a washing buffer substantially comprising 0.5×SSC (150 mM NaCl; 15 mM sodium citrate) and 0.1% SDS at 65° C.

In this specification, the percentage of "identity", "homology" and "similarity" between sequences (such as amino acid or nucleotide sequences) is determined by comparing two sequences optionally aligned in a comparison window. In comparison with a standard sequence for the optimum alignment of two sequences (it is assumed that although gaps may be generated when additions are contained in another sequence, the standard sequence herein does not have additions or deletions), additions or deletions (that is, gaps) can be included in the comparison window of polynucleotide sequences or polypeptide sequences. By determining the number of positions at which the same nucleic acid base or amino acid residue is recognized in both the sequences, the number of matched positions is determined, and the number of matched positions is divided by the number of positions in total in the comparison window and then multiplied by 100 to determine percentage identity. When used in a search, a suitable sequence comparison algorithm and program are selected from those well-known in the art, in order to evaluate homology. Such algorithms and programs include, but are not limited to, TBLASTN, BLASTP, FASTA, TFASTA and CLUSTALW (Pearson and Lipman, 1988, Proc. Natl. Acad. Sci. USA 85(8):2444-2448, Altschul et al., 1990, J. Mol. Biol. 215(3):403-410, Thompson et al., 1994, Nucleic Acids Res. 22(2):4673-4680, Higgins et al., 1996, Methods Enzymol. 266:383-402, Altschul et al., 1990, J. Mol. Biol. 215(3):403-410, Altschul et al., 1993, Nature Genetics 3:266-272). In a particularly preferable embodiment, the homology between protein sequences or nucleic acid sequences is evaluated by using Basic Local Alignment Search Tool (BLAST) known in the art (see, for example, Karlin and Altschul, 1990, Proc. Natl. Acad. Sci. USA 87:2267-2268, Altschul et al., 1990, J. Mol. Biol. 215:403-410, Altschul et al., 1993, Nature Genetics 3:266-272, Altschul et al., 1997, Nuc. Acids Res. 25:3389-3402). Particularly, five special BLAST programs can be used to perform the following operations to compare or search:

(1) comparison, by BLASTP and BLAST3, of an amino acid query sequence with a protein sequence database;
(2) comparison, by BLASTN, of a nucleotide query sequence with a nucleotide sequence database;
(3) comparison, by BLASTX, of a conceptual translation product into which the nucleotide query sequence (both strands) was converted in 6 reading frames, with a protein sequence database;
(4) comparison, by TBLASTN, of the protein query sequence with a database of nucleotide sequences converted in all 6 reading frames (both strands); and
(5) comparison, by TBLASTX, of the nucleotide query sequence converted in 6 reading frames, with a database of nucleotide sequences converted in 6 reading frames.

The BLAST program is a program by which between an amino acid query sequence or a nucleic acid query sequence and a subject sequence, obtained preferably from a protein sequence database or a nucleic acid sequence database, a similar segment called "high-score segment pair", is specified, thereby identifying a homologous sequence. Preferably, the high-score segment pair is identified (that is, aligned) by scoring matrices, many of which are well-known in the art. Preferably, BLOSUM62 matrix (Gonnet et al., 1992, Science 256:1443-1445, Henikoff and Henikoff, 1993, Proteins 17:49-61) is used as the scoring matrix. PAM or PAM250 matrix, though not preferable to this matrix, can also be used (see, for example, Schwartz and Dayhoff, eds., 1978, Matrices for Detecting Distance Relationships: Atlas of Protein Sequence and Structure, Washington: National Biochemical Research Foundation). By using the BLAST program, the statistical significance of every identified high-score segment pair is evaluated to select preferably a segment satisfying a threshold level of significance established individually by the user, such as the degree of homology unique to the user. The statistical significance of the high-score segment pair is evaluated preferably using a Karlin formula for determining statistical significance (see Karlin and Altschul, 1990, Proc. Natl. Acad. Sci. USA 87:2267-2268).

(Modification of Gene, Protein Molecule, Nucleic Acid Molecule and the Like)

A specific amino acid contained in a sequence of a specific protein molecule can be substituted by another amino acid in, for example, a protein structure such as a cationic region or a substrate molecule-binding site, without resulting in evident reduction or loss in the interaction binding ability of the protein. The biological functions of a certain protein are determined by the interaction ability and properties thereof. Accordingly, substitution of specific amino acid(s) can be made in an amino acid sequence or at the level of its DNA coding sequence, and a protein generated by such substitution can still maintain its original properties. Accordingly, various modifications can be carried out in a peptide disclosed in this specification or the corresponding DNA encoding the peptide, without resulting in evident loss in biological utility.

In designing the variants described above, the amino acid hydrophobicity index can be taken into consideration. The importance of the hydrophobic amino acid index in facilitating interactive biological functions in proteins is recognized generally in the art (Kyte, J and Doolittle, R. F. J. Mol. Biol. 157(1):105-132, 1982). The hydrophobicity of amino acids contributes to a secondary structure of a generated protein and defines the interaction between the protein with other molecules (for example, an enzyme, substrate, receptor, DNA, antibody, antigen and the like). Each amino acid is assigned a hydrophobicity index based on its hydrophobicity and charge properties, as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamic acid (−3.5); glutamine (−3.5); aspartic acid (−3.5); asparagine (−3.5); lysine (−3.9); and arginine (−4.5).

It is well known in the art that a specific amino acid can be substituted by another amino acid having similar hydrophobicity index to generate a protein still having similar biological functions (for example, a protein equivalent in enzyme activity). In such an amino acid substitution, the hydrophobicity index is preferably within ±2, more preferably within ±1, still more preferably within ±0.5. It is appreciated in the art that such amino acid substitution based on hydrophobicity is effective.

In designing variants, hydrophilicity index can also be considered by those skilled in the art. As described in U.S. Pat. No. 4,554,101, the following hydrophilicity index is assigned to amino acid residues: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is appreciated that a specific amino acid can be substituted by another amino acid having a similar hydrophilicity index to give a biological equivalent. In such amino acid substitution, the hydrophilicity index is preferably within ±2, more preferably within ±1, still more preferably within ±0.5.

As used herein, "conservative substitution" refers to amino acid substitution in which an original amino acid and a substituting amino acid are similar to each other in respect the hydrophilicity index and/or hydrophobicity index, as described above. For example, amino acids substituted by each other in conservative substitution include, but are not limited to, those with hydrophilicity index or hydrophobicity index within ±2, preferably within ±1, more preferably within ±0.5. Accordingly, examples of the conservative substitution are well-known to those skilled in the art and include, but are not limited to, substitutions between the following amino acids of each group: arginine and lysine; glutamic acid and aspartic acid; serine and threonine; glutamine and asparagine; and valine, leucine, and isoleucine.

As used herein, a "variant" refers to a substance derived from the original polypeptide or polynucleotide by partial modification. Such variants include, but are not limited to, substituted variants, added variants, deleted variants, truncated variants, allelic variants, and the like. Such variants include, but are not limited to, those having one or several substitutions, additions and/or deletions, or one or more substitutions, additions and/or deletions in their nucleic acid molecule or polypeptide standard. Alleles refer to genetic variants belonging to the same gene locus which are discriminated from each other. Accordingly, the term "allelic mutants" refers to those variants in the relationship of alleles to a certain gene. Such an allelic mutant usually has a sequence identical or extremely similar to its corresponding allele and usually has almost the same biological activity, but may rarely have a different biological activity. The term "species homolog" or "homolog" refers to a sequence which in a certain species, has homology (preferably 60% or more, more preferably 80% or more, 85% or more, 90% or more, or 95% or more homology) with a certain gene at the amino acid or nucleotide level. The method of obtaining such a species homolog is evident from the description of this specification. An "ortholog" is also called an orthologous gene, which refers to two genes derived from a common ancestor by species differentiation. For example in a hemoglobin gene family having a multigene structure, human and mouse α-hemoglobin genes are in the relationship of orthologs, while human α-hemoglobin gene and human β-hemoglobin gene are in the relationship of paralog (genes occurring upon gene duplication). Orthologs are useful for estimation of a molecular genealogical tree. Because the ortholog in another species can usually have similar functions as in the original species, the ortholog of the present invention can also be useful in the present invention.

In this specification, the term "conservative variant" or "conservatively modified variant" can be applied to both amino acid sequences and nucleic acid sequences. A conservative variant of a specific nucleic acid sequence refers to a nucleic acid encoding the same or substantially the same amino acid sequence, or to substantially the same sequence as the specific nucleic acid when the nucleic acid does not encode an amino acid sequence. Because of the degeneracy of genetic code, a large number of functionally identical nucleotide sequences encode any predetermined protein sequences. For example, all of the codons GCA, GCC, GCG and GCU encode the amino acid alanine. Thus, in every position where alanine is specified by its codon, the codon can be changed into arbitrary one of the corresponding codons shown above, without changing the encoded polypeptide. Such change in nucleic acid is "silent variant (mutation)", that is, one conservatively modified mutation. Every polypeptide-coding nucleotide sequence herein contains its possible every silent mutation. It is understood in the art that each codon (excluding AUG which is usually the sole codon encoding methionine and TGG which is usually the sole codon encoding tryptophan) in a nucleic acid can be modified to produce functionally identical molecules. Accordingly, each silent mutation in a nucleic acid encoding a polypeptide is implicitly contained in each described sequence. Preferably, such modification can be achieved so as to avoid substitution of cysteine which is an amino acid having significant effects on the higher-order structure of a polypeptide. The method of modifying such nucleotide sequences includes treatments such as cleavage with restriction enzymes, ligation by treatment with DNA polymerase, Klenow fragment, and DNA ligase, and the like, and site-specific nucleotide substitution with a synthetic oligonucleotide and the like (site-directed mutagenesis; Mark Zoller and Michael Smith, Methods in Enzymology, 100, 468-500 (1983)), and methods usually used in the field of molecular biology can also be used in modification.

For preparing functionally equivalent polypeptides in this specification, not only the substitution of amino acids but also the addition, deletion or modification of amino acids can be carried out. The substitution of amino acids means that the original peptide is substituted with one or more amino acids, for example, 1 to 10 amino acids, preferably 1 to 5 amino acids and more preferably 1 to 3 amino acids. The addition of amino acids means that one or more amino acids, for example, 1 to 10 amino acids, preferably 1 to 5 amino acids and more preferably 1 to 3 amino acids are added to the original peptide strand. The deletion of amino acids means that one or more amino acids, for example, 1 to 10 amino acids, preferably 1 to 5 amino acids and more preferably 1 to 3 amino acids are deleted from the original peptide. The modification of amino acids includes, but is not limited to, amidation, carboxylation, sulfation, halogenation, truncation, lipidation, phosphorylation, alkylation, glycosylation, phosphorylation, hydroxylation, and acylation (for example, acetylation). The amino acids to be substituted or added may be naturally occurring amino acids or may be non-natural amino acids or amino acid analogs. Naturally occurring amino acids are preferable.

The term "peptide analog" or "peptide derivative" as used herein refers to a compound different from the peptide but equivalent in at least one chemical function or biological function to the peptide. Accordingly, the peptide analog contains one or more amino acid analogs or amino acid derivatives added to, or substituted on, the original peptide. The peptide analog has been subjected to the addition or substitution such that its functions become substantially similar to the functions of the original peptide (for example, the peptide analog and the original peptide are similar in pKa value, functional group, mode of bonding to another molecule, and water solubility). Such peptide analogs can be prepared by using techniques well-known in the art. Accordingly, the peptide analog can be a polymer containing amino acid analog(s).

A composition of a chemically modified polypeptide, which has the polypeptide of the present invention bound to a polymer, falls within the scope of the invention. This polymer can be water-soluble and can prevent the protein from being precipitated in an aqueous environment (for example, a physiological environment). Suitable aqueous polymers can be selected for example, from the group consisting of polyethylene glycol (PEG), monomethoxy polyethylene glycol, dextran, cellulose, a polymer based on other carbohydrates, poly (N-vinyl pyrrolidone)polyethylene glycol, a polypropylene glycol homopolymer, a polypropylene oxide/ethylene oxide copolymer, polyoxyethylated polyol (for example, glycerol) and polyvinyl alcohol. Usually, this selected polymer is modified, has a single reaction group (for example, an active ester for acylation or aldehyde for alkylation), and can thus have a regulated degree of polymerization. The polymer can have any molecular weight and may be branched or not branched, and a mixture of such polymers can also be used. As the chemically modified polymer of the present invention, a pharmaceutically acceptable polymer is selected when it is to be therapeutically used.

When this polymer is to be modified by an acylation reaction, this polymer should have a single reactive ester group. Alternatively, when this polymer is to be modified by reductive alkylation, this polymer should have a single reactive aldehyde group. The reactive aldehyde is preferably polyethylene glycol, propionaldehyde (propionaldehyde is water-soluble) or its mono C1 to C10 alkoxy or aryloxy derivative (see, for example, U.S. Pat. No. 5,252,714, the disclosure of which is expressly incorporated herein by reference in its entirety).

The pegylation of the polypeptide of the present invention can be carried out by any pegylation reaction known in the art, as shown in, for example, the following references: Focus on Growth Factors 3, 4-10 (1992), EP 0 154 316, and EP 0 401 384, the disclosure of which is expressly incorporated herein by reference in their entirety. Preferably, this pegylation is carried out via an acylation reaction or alkylation reaction with a reactive polyethylene glycol molecule (or a similar reactive water-soluble polymer). The water-soluble polymer for pegylation of the polypeptide of the present invention is polyethylene glycol (PEG). As used herein, the "polyethylene glycol" encompasses any forms of PEG, wherein the PEG is used for derivatising the polypeptide of the invention into another protein (for example, mono (C1 to C10) alkoxy polyethylene glycol or mono (C1 to C10) aryloxy polyethylene glycol).

The chemical derivatization of the polypeptide of the present invention can be carried out under conditions suitable for reacting the biologically active substance with an activated polymer molecule. Generally, the method of preparing the pegylated polypeptide of the present invention comprises (a) reacting polyethylene glycol (for example, a reactive ester or aldehyde derivative of PEG) with the polypeptide under conditions where the polypeptide binds to one or more groups in PEG, and (b) obtaining this reaction product. On the basis of known parameters and desired results, it is easy for those skilled in the art to select optimum reaction conditions or acylation reaction.

The pegylated polypeptide of the present invention can be used generally for treating a condition which can be ameliorated or controlled by administering the polypeptide described in this specification, and the chemically derived polypeptide of the present invention disclosed herein, and can have a further activity, an increased or decreased biological activity or other features (for example, an increased or decreased half-life), as compared with its original non-derived molecule. The polypeptide of the present invention, fragments, variants, and derivatives thereof can be used alone, simultaneously, or in combination with another pharmaceutical composition. Such cytokines, growth factors, antigens, anti-inflammatory agents and/or chemotherapeutic agents are suitable for treating symptoms.

Similarly, the "polynucleotide analog" or "nucleic acid analog" refers to a compound different from the original polynucleotide or nucleic acid but equivalent to the polynucleotide or nucleic acid in respect of at least one chemical or biological function. Accordingly, the polynucleotide analog or nucleic acid analog includes compounds having one or more nucleotide analogs or nucleotide derivatives added to, or substituted on, the original peptide.

In the nucleic acid molecule used in this specification, a part of the nucleic acid sequence may be deleted, may be substituted by other bases, or may have another nucleic acid sequence inserted partially into it, as described above, as long as its expressed polypeptide has substantially the same activity as that of the natural polypeptide. Alternatively, another nucleic acid may be bound to the 5'- and/or 3'-terminal. The nucleic acid molecule may be a molecule hybridizing with a gene encoding the polypeptide under stringent conditions and encoding a polypeptide having substantially the same functions as those of the polypeptide. Such gene is known in the art and can be utilized in the present invention.

Such nucleic acid can be obtained by the well-known PCR method or can be chemically synthesized. These methods can be combined with, for example, a site-directed mutagenesis method, hybridization method and the like.

In this specification, the "substitution, addition or deletion" of the polypeptide or polynucleotide refers to the substitution, addition or deletion wherein amino acid(s) or a substitute therefor or nucleotide(s) or a substitute therefor is substituted on, added to, or deleted from, the original polypeptide or polynucleotide. Techniques for such substitution, addition or deletion are well-known in the art and examples of such techniques include site-directed mutagenesis and the like. As long as the number of amino acids or nucleotides to be substituted, added or deleted is 1 or more, the number thereof may be any number, and as long as objective functions (for example, an ability of signal transduction of hormone or cytokine) can be retained by the polypeptide or polynucleotide variant by such substitution, addition or deletion, the number thereof can be increased. For example, the number can be one or several, preferably within 20%, within 10%, or can be 100 or less, 50 or less, 25 or less.

(Genetic Engineering)

A polypeptide having the amino acid sequence of SEQ ID NO: 2 used in the present invention, a fragment thereof and a variant thereof can be produced by genetic engineering techniques.

The "recombinant vector" for prokaryotic cells usable in the present invention is exemplified by pcDNA3(+), pBluescript-SK(+/−), pGEM-T, pEF-BOS, pEGFP, pHAT, pUC18, and pFT-DEST™ 42GATEWAY (Invitrogen) and the like.

The "recombinant vector" for animal cells usable in the present invention is exemplified by pcDNAI/Amp, pcDNAI, pCDM8 (all of which are commercially available from Funakoshi), pAGE107 [Japanese Laid-Open Publication No. 3-229 (Invitrogen), pAGE103 [J. Biochem., 101, 1307 (1987)], pAMo, pAMoA [J. Biol. Chem., 268, 22782-22787 (1993)], a retrovirus type expression vector based on murine stem cell virus (MSCV), pEF-BOS, and pEGFP and the like.

Potent promoters for expression in mammalian cells include, for example, various natural promoters (for example, SV40 early promoter, adenovirus E1A promoter, human cytomegalovirus (CMV) promoter, human elongation factor-1 (EF-1) promoter, *Drosophila* minimum heat shock protein 70 (HSP) promoter, human metallothionein (MT) promoter, Rouse sarcoma virus (RSV) promoter, human ubiquitin C (UBC) promoter, human actin promoter) and artificial promoters (for example, fusion promoters such as SRα promoter (fusion of SV40 early promoter and HTLV LTR promoter), CAG promoter (hybrid between CMV-IE enhancer and chicken actin promoter) and the like) are well-known, and thus these well-known promoters or variants thereof can be used to easily increase expression levels in recombinant expression.

When *Escherichia coli* is used as the host cell, such a promoter can include promoters derived from *Escherichia coli* and phage, such as trp promoter (Ptrp), lac promoter (Plac), PL promoter, PR promoter, PSE promoter and the like, as well as SPO1 promoter, SPO2 promoter, penP promoter and the like. It is also possible to use artificially designed and modified promoters such as a promoter having two Ptrp tandemly connected (Ptrp×2), tac promoter, lacT7 promoter, and let I promoter.

The terms "operatively linked" as used herein means that the nucleotide sequence is arranged under the control of transcription translation regulatory sequences (for example, a promoter, enhancer and the like) or a translation regulatory sequence so as to bring about desired expression (that is, operation). For linking the promoter operatively with the gene, the promoter is usually placed just upstream of the gene, but may not necessarily be placed adjacent to the gene.

In this specification, techniques of introducing the nucleic acid molecule into a cell may be any technique and include, for example, transformation, transduction, transfection and the like. Such techniques of introducing the nucleic acid molecule are well known in the art and routinely used, and are described in, for example, Ausubel F. A. et al. (ed.) (1988), Current Protocols in Molecular Biology, Wiley, New York, N.Y.; Sambrook J. et al. (1987) Molecular Cloning: A Laboratory Manual, 2nd Ed., and 3rd Ed., Cold Spring Harbor Laboratory Press, Cold Spring Harbor, N.Y.; and BESSATSU GIKKEN-IGAKU (Experimental Medicine, Separate Volume), "IDENSHI-DOUNYU & HATSUGEN-KAISEKI ZIKKEN-HOU (Experimental Methods of Gene Introduction & Expression Analysis)", published by Yodosha, 1997. The introduction of the gene can be confirmed by the methods described in this specification, such as Northern blotting or Western blotting analysis or other well-known routine methods.

As the method of introducing the vector, any of the above-described methods of introducing DNA into a cell can be used, and include transfection, transduction, transformation and the like (for example, a calcium phosphate method, a liposome method, a DEAE dextran method, an electroporation method, a method using a particle gun (gene gun), and the like).

When prokaryotic cells are used in genetic manipulation in the present invention, examples of such prokaryotic cells include prokaryotic cells belonging to the genera *Escherichia, Serratia, Bacillus, Brevibacterium, Corynebacterium, Microbacterium* and *Pseudomonas*, for example *Escherichia coli* XL1-Blue, *Escherichia coli* XL2-Blue, and *Escherichia coli* DH1.

As used herein, the animals cells include mouse myeloma cells, rat myeloma cells, mouse hybridoma cells, Chinese hamster CHO cells, BHK cells, African green monkey kidney cells, human leukemic cells, HBT5637 (Japanese Laid-Open Publication No. 63-299), and a human colon cancer strain, and the like. Mouse myeloma cells include ps20, NSO and the like; rat myeloma cells include YB2/0 and the like; human fetus kidney cells include HEK293 (ATCC: CRL-1573) and the like; human leukemic cells include BALL-1 and the like; African green monkey kidney cells include COS-1 and COS-7; human colon cancer cell strain includes HCT-15, human neuroblastomas includes SK—N—SH and SK—N—SH-5Y, mouse neuroblastoma Neuro2A, and the like.

As used herein, the method of introducing the recombinant vector includes any method of introducing DNA and includes, for example, a calcium chloride method, an electroporation method (Methods. Enzymol., 194, 182 (1990)), a lipofection method, a spheroplast method (Proc. Natl. Acad. Sci. USA, 84, 1929 (1978)), an lithium acetate method (J. Bacteriol., 153, 163 (1983)), and a method described in Proc. Natl. Acad. Sci. USA, 75, 1929 (1978).

In this specification, the method of infection with retrovirus is well-known in the art as described in, for example, Current Protocols in Molecular Biology supra (particularly Units 9.9-9.14); a sufficient amount of infected cells can be obtained for example by trypsinizing embryonic stem cells to form a single-cell suspension and then co-culturing the cells together with a culture supernatant of virus-producing cells (packaging cell lines) for 1 to 2 hours.

Transient expression of Cre enzyme, DNA mapping on chromosome, and the like, used in the method of removing the genome or gene locus used in the present invention, are well-known in the art as described in SAIBOU-KOGAKU BESSATSU ZIKKEN PUROTOKORU SIRIZU (Cell Engineering Experimental Protocol Series, Separate Volume) "FISH ZIKKEN PUROTOKORU HITO-GENOMU KAISEKI KARA SENSYOKUTAI-IDENSI SHINDAN MADE (FISH Experimental Protocol from Human Genome Analysis to Chromosome/Gene Diagnosis)", supervised by Kenichi Matsubara & Hiroshi Yoshikawa and published by Shujunsha (Tokyo, JP).

As used herein, the "kit" refers to a product containing a plurality of vessels and manufacture's instructions, wherein the vessels contain the pharmaceutical composition of the invention, other agents, and a carrier, respectively.

In this specification, the "pharmacologically acceptable carrier" is a substance used in producing pharmaceutical preparations or agricultural chemicals, such as animal drugs, which do not adversely affect the active ingredient. For example, such pharmaceutically acceptable carriers includes, but are not limited to, an antioxidant, preservative, coloring agent, flavor, diluent, emulsifier, suspending agent, solvent, filler, bulking agent, buffer agent, delivery vehicle, excipient and/or pharmaceutical adjuvant.

Those skilled in the art can easily determine the type and amount of the pharmacological agent used in the treatment method of the present invention, on the basis of information (for example, information on disease) obtained by the method of the present invention and in consideration of the intended use, objective disease (type, severity, and the like), the age, weight, sex and past illnesses of the patient and the form or type of the site to which the agent is administered. The frequency at which the monitoring method of the invention is applied to a subject (or a patient) can also be determined easily by those skilled in the art in consideration of the intended use, objective disease (type, severity, and the like), the age, weight, sex and past illnesses of the patient, and the therapeutic process. The frequency of monitoring the state of disease is for example once per day to once per several months (for example, once per week to once per month). Monitoring is performed preferably once per week or once per month, while the progress is observed.

If necessary, two or more agents can be used in the therapy of the present invention. When two or more agents are used, agents having similar properties or derived from the same origin or agents having different properties or derived from different origins may be used. Information about disease levels for the method of administering two or more agents can also be obtained by the method of the present invention.

Description of Preferred Embodiments

Hereinafter, preferable embodiments are described, and it should be appreciated that these embodiments are merely illustrative of the invention and the scope of the invention is not limited to such preferred embodiments. It should also be appreciated that those skilled in the art can easily make modifications, alterations and the like within the scope of the invention by reference to the following preferable examples.

(Process for Producing the Polypeptide)

A transformant derived from a microorganism, an animal cell and the like and harboring a recombinant vector into which a DNA encoding the polypeptide of the present invention has been integrated is cultured according to a usual culture method, to generate and accumulate the polypeptide of the present invention, and the polypeptide of the present invention is collected from the culture of the present invention, whereby the polypeptide of the present invention can be produced.

The method of culturing the transformant of the present invention in a medium can be carried out according to a usual method used in culturing its host. The medium for culturing the transformant obtained by using, as the host, prokaryotes such as *Escherichia coli* and the like or eukaryotes such as yeasts and the like may be either a natural medium or a synthetic medium as long as the medium contains a carbon source, a nitrogen source, inorganic salts and the like assimilable by the living organism of the present invention and can be used in efficiently culturing the transformant.

The carbon source must be capable of assimilation by the respective microorganisms, and glucose, fructose, sucrose, molasses containing these sugars, carbohydrates such as starch or starch hydrolysates, organic acids such as acetic acid, propionic acid and the like, and alcohols such as ethanol, propanol and the like can be used as the carbon source.

As the nitrogen source, it is possible to use ammonia, ammonium salts of inorganic or organic acids, such as ammonium chloride, ammonium sulfate, ammonium acetate, ammonium phosphate and the like, other nitrogen-containing substances, peptone, meat extract, yeast extract, corn steep liquor, casein hydrolysates, bean cake, bean cake hydrolysates, various fermentation microorganisms, and digested materials thereof.

As the inorganic salt, it is possible to employ potassium hydrogenphosphate, dipotassium hydrogenphosphate, magnesium phosphate, magnesium sulfate, sodium chloride, ferrous sulfate, manganese sulfate, copper sulfate, calcium carbonate, and the like. Culture is carried out under aerobic conditions, for example in a shake culture or in stirred culture under aeration.

The culture temperature is preferably 15 to 40° C., and the culture time is usually 5 hours to 7 days. During culture, the pH is kept at 3.0 to 9.0. Adjustment of the pH is carried out by using an inorganic or organic acid, an alkali solution, urea, calcium carbonate, ammonia, and the like. During culture, an antibiotic such as ampicillin or tetracycline may be added to the medium, if necessary.

When the microorganism transformed with an expression vector using an inducible promoter is cultured, an inducer may be added if necessary to the medium. For example, isopropyl-β-D-thiogalactopyranoside or the like is added to the medium where the microorganism transformed with an expression vector using lac promoter is cultured, or indole acrylic acid or the like may be added to the medium where the microorganism transformed with an expression vector using trp promoter is cultured. Cells or organs into which the gene was introduced can be cultured on a large scale in a pot fermenter.

For example, when animal cells are used, the medium used in culturing the cells of the present invention includes generally used mediums such as RPMI1640 medium (The Journal of the American Medical Association, 199, 519 (1967)), Eagle's MEM medium (Science, 122, 501 (1952)), DMEM medium (Virology, 8, 396 (1959)), 199 medium (Proceedings of the Society for the Biological Medicine, 73, 1 (1950)), or media prepared by adding fetal bovine serum and the like to the above mediums.

Culture is carried out usually at pH 6 to 8, at 25 to 40° C. in the presence of 5% $CO_2$ for 1 to 7 days. If necessary, antibiotics such as kanamycin, penicillin, streptomycin and the like may be added to the medium.

For isolating or purifying the polypeptide of the present invention from a culture of the transformant transformed with a nucleic acid sequence encoding the polypeptide of the present invention, usual enzyme isolation or purification methods that are well-known and routine in the art can be used. For example, when the polypeptide of the present invention is secreted extracellularly from the transformant for production of the polypeptide of the present invention, the culture is treated by techniques such as centrifugation and the like, to obtain a soluble fraction. From the soluble fraction, a purified preparation can be obtained by techniques such as solvent extraction, salting out with ammonium sulfate or the like, desalting, precipitation with an organic solvent, anion exchange chromatography on resin such as diethylaminoethyl (DEAE)-Sepharose, DIAION HPA-75 (Mitsubishi Chemical Corporation) and the like, cation exchange chromatography on resin such as S-Sepharose FF (Pharmacia) and the like, hydrophobic chromatography on resin such as butyl Sepharose, phenyl Sepharose and the like, gel filtration through a molecular sieve, affinity chromatography, and electrophoresis such as chromatofocusing, isoelectric focusing, and the like.

When the polypeptide of the present invention is accumulated in a solubilized state in cells of the transformant for production of the polypeptide of the present invention, the culture is centrifuged to collect the cells from the culture, then the cells are washed and then disrupted with a sonicator, a French press, a Manton-Gaulin homogenizer, Dyno Mill and the like to obtain a cell-free extract. From a supernatant obtained by centrifuging the cell-free extract, a purified preparation can be obtained by techniques such as solvent extraction, salting out with ammonium sulfate or the like, desalting, precipitation with an organic solvent, anion exchange chromatography on resin such as diethylaminoethyl (DEAE)-Sepharose, DIAION HPA-75 (Mitsubishi Chemical Corporation) and the like, cation exchange chromatography on resin such as S-Sepharose FF (Pharmacia) and the like, hydrophobic chromatography on resin such as butyl Sepharose, phenyl Sepharose and the like, gel filtration using a molecular sieve, affinity chromatography, and electrophoresis such as chromatofocusing, isoelectric focusing, and the like.

When the polypeptide of the present invention is expressed to form an insoluble body in cells, the cells are recovered, disrupted and centrifuged in the same manner as above to give a precipitated fraction, from which the polypeptide of the present invention is recovered by a usual method, and the insolubilized polypeptide thus obtained is solubilized with a polypeptide denaturant. The resulting solubilized solution is diluted or dialyzed, to provide a dilute solution such that the polypeptide denaturant is free or the concentration of the polypeptide denaturant is decreased to such a degree as not to cause denaturation of the polypeptide, thereby constituting a normal stereostructure of the polypeptide of the present invention, followed by isolating and purifying it by the same methods as described above, to give a purified preparation.

The polypeptide can also be purified according to a usual protein purification method [J. Evan. Sadler et al.: Methods in Enzymology, 83, 458]. Alternatively, the polypeptide of the present invention can be produced as a fusion protein with another protein and purified by affinity chromatography containing a substance having affinity to the fusion protein [Akio Yamakawa, ZIKKENIGAKU (Experimental Medicine), 13, 469-474 (1995)]. For example, the polypeptide of the present invention can be produced as a fusion protein with protein A and purified by affinity chromatography containing immunoglobulin G according to a method of Lowe et al. [Proc. Natl. Acad. Sci., USA, 86, 8227-8231 (1989), Genes and Develop., 4, 1288 (1990)].

Alternatively, the polypeptide of the present invention can be produced as a fusion protein with FLAG peptide and purified by affinity chromatography containing an anti-FLAG antibody [Proc. Natl. Acad. Sci., USA, 86, 8227 (1989), Genes Develop., 4, 1288 (1990)]. For such fusion proteins, a proteolysis cleavage site is introduced into a connecting site between the fusion portion and the recombinant protein in the expression vector in order to enable separation of the recombinant protein from the fusion portion, following purification of the fusion protein. Such enzymes (and homologous) recognition sites include factor Xa, thrombin and enterokinase. Typical fusion vectors include pGEX (Pharmacia Biotech; Smith and Johnson (1988) Gene 67, 31-40), pMAL (New England Biolabs, Beverly, Mass.), and pRIT5 (Pharmacia, Piscataway, N.J.), by which glutathione-S-transferase (GST), maltose E-binding protein, and protein A are fused respectively with the target recombinant protein.

The polypeptide of the present invention can also be purified by affinity chromatography using an antibody against the polypeptide itself. The polypeptide of the present invention can be produced by using an in vitro transcription/translation system according to known methods [J. Biomolecular NMR, 6, 129-134, Science, 242, 1162-1164, J. Biochem., 110, 166-168 (1991)].

On the basis of information about the amino acid sequence, the polypeptide of the present invention can be produced by chemical synthesis methods such as Fmoc method (fluorenyl methyloxy carbonyl method), tBoc method (t-butyloxy carbonyl method) and the like. The polypeptide can also be chemically synthesized by utilizing peptide synthesizers from Advanced Chem Tech, Applied Biosystems, Pharmacia Biotech, Protein Technology Instrument, Synthecell-Vega, PerSeptive, Shimadzu Corporation, and the like.

The structural analysis of the purified polypeptide of the present invention can be carried out by methods usually used in protein chemistry, for example by methods described in IDENSHI KURONINGU NO TAMENO TANNPA-KUSITSU KOUZOU KAISEKI (protein structural analysis for genetic cloning) (authored by Hisashi Hirano, published by Tokyo Kagaku Dojin, 1993). The physiological activity of the polypeptide of the present invention can be measured according to known measurement methods.

The production of soluble polypeptide useful in the present invention can also be accomplished by various methods known in the art. For example, the polypeptide can be derived from the intact polypeptide molecule by proteolysis using a specific endopeptidase in combination with an exopeptidase and/or Edman degradation. This intact polypeptide molecule can be purified from its natural source using conventional methods. Alternatively, the intact polypeptide can be generated by recombinant DNA technology utilizing cDNA, expression vector, and well-known techniques for expressing the recombinant gene.

Preferably, the soluble polypeptide useful in the present invention is produced directly and thus eliminates the necessity for the whole polypeptide as a starting material. This can be achieved by conventional chemical synthesis techniques or by well-known recombinant DNA techniques (wherein only the DNA sequence encoding the desired peptide is expressed in a transformed host). For example, the gene encoding the desired soluble polypeptide can be synthesized by chemicals means using an oligonucleotide synthesizer. Such an oligonucleotide is designed based on the amino acid sequence of the desired soluble polypeptide. The specific DNA sequence encoding the desired peptide can also be derived from the full-length DNA sequence by isolation of a specific restriction endonuclease fragment or by PCR synthesis of a specific region from cDNA.

(Method of Preparing the Mutant Polypeptide)

The amino acid deletion, substitution or addition (including fusion) of the polypeptide of the present invention can be carried out by site-directed mutagenesis well-known in the art. Such substitution, addition or deletion of one or more amino acids can be carried out according to methods described in Molecular Cloning, A Laboratory Manual, Second Edition, Cold Spring Harbor Laboratory Press (1989), Current Protocols in Molecular Biology, Supplement 1-38, John Wiley & Sons (1987-1997), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci USA, 82, 488 (1985), Proc. Natl. Acad. Sci., USA, 81, 5662 (1984), Science, 224, 1431 (1984), PCT WO85/00817 (1985), Nature, 316, 601 (1985) and the like.

(Synthesis Chemistry)

The factors such as peptides, chemical substances and small molecules described in this specification can be synthesized using synthetic chemistry techniques. As synthetic chemical techniques, techniques well-known in the art can be used. For such synthetic chemical techniques, for example, Fiesers' Reagents for Organic Synthesis (Fieser's Reagents for Organic Synthesis) Tse-Lok Ho, John Wiley & Sons Inc (2002) can be referred to.

The factor of the present invention when utilized as a compound can be used in the form of a salt. The "salt" is preferably a pharmaceutically acceptable salt and includes, for example, a salt with an inorganic base, a salt with an organic base, a salt with an inorganic acid, a salt with an organic acid and a salt with a basic or acidic amino acid. The salt with an inorganic base includes alkali metal salts such as sodium salt, potassium salt and the like, and alkaline earth metal salts such as calcium salt, magnesium salt, barium salt and the like, as well as aluminum salt, ammonium salt and the like. The salt with an organic base includes salts with trimethylamine, triethylamine, pyridine, picoline, ethanolamine, diethanolamine, triethanolamine, dicyclohexylamine, N,N'-dibenzyl ethylene diamine, and the like. The salt with an inorganic acid includes salts with hydrochloric acid, hydrofluoric acid, hydrogen bromide, nitric acid, sulfuric acid, phosphoric acid, perchloric acid, hydriodic acid, and the like. The salt with an organic acid includes salts with formic acid, acetic acid, trifluoroacetic acid, fumaric acid, oxalic acid, tartaric acid, maleic acid, citric acid, succinic acid, malic acid, mandelic acid, ascorbic acid, lactic acid, gluconic acid, methanesulfonic acid, p-toluenesulfonic acid, benzene sulfonic acid and the like. The salt with a basic amino acid includes salts with arginine, lysine, ornithine and the like, and the salt with an acidic amino acid includes salts with aspartic acid, glutamic acid and the like.

When the factor of the present invention is utilized as a compound, it can be used in the form of a hydrate. The "hydrate" is preferably a pharmacologically acceptable hydrate and also includes hydrous salts, and specific examples include monohydrate, dihydrate, hexahydrate and the like.

(Immuno Chemistry)

The production of an antibody recognizing the polypeptide of the present invention is also well-known in the art. For example, the preparation of a polyclonal antibody can be carried out by administering, as the antigen, a purified preparation of the obtained full-length polypeptide or a partial fragment thereof, or a peptide having a partial amino acid sequence of the protein of the present invention, to an animal.

When the antibody is to be produced, a rabbit, goat, rat, mouse, hamster, and the like, can be used as the animal to which the antigen is administered. The amount of the antigen administered is preferably 50 to 100 µg per animal. When the peptide is used, the peptide is used as the antigen desirably after it is covalently bound to a carrier protein such as keyhole limpet hemocyanin or bovine thyroglobulin. The peptide used as antigen can be synthesized by a peptide synthesizer. The peptide is administered 3 to 10 times at 1- to 2-week intervals after the first administration. Three to seven days after each administration, blood is collected from a fundus venous plexus, and whether the serum reacts with the antigen used in the immunization is confirmed by an enzyme-linked immunosorbent assay ["Koso Meneki Sokuteiho" (ELISA method) published by Igaku-Shoin Ltd., 1976, and Antibodies—A Laboratory Manual, Cold Spring Harbor Laboratory (1988)], and the like.

Serum is obtained from a non-human mammal having serum showing a sufficient antibody titer against the antigen used in the immunization, and from this serum, a polyclonal antibody can be separated and purified by well-known methods. The preparation of a monoclonal antibody is also well-known in the art. For preparing antibody-producing cells, a rat having serum showing a sufficient antibody titer against a partial fragment polypeptide of the polypeptide of the invention used in the immunization is used as a source of antibody-producing cells, and the cells are fused with myeloma cells to produce hybridomas. Thereafter, a hybridoma specifically reacting with a partial fragment polypeptide of the polypeptide of the invention is selected by ELISA method. A monoclonal antibody produced by the hybridoma obtained in this manner can be used for various purposes.

Such antibody can be used for example in a method for immunological detection of the polypeptide of the present invention, and a method for immunological detection of the polypeptide of the present invention, wherein the antibody of the present invention is used, can include an ELISA method/fluorescent antibody method using a microtiter plate, a western blotting method, an immune histological staining method, and the like.

The antibody can also be used in a method of immunologically quantifying the polypeptide of the present invention. The method of quantifying the polypeptide of the present invention can include a sandwich ELISA method using two kinds of monoclonal antibodies which amongst those antibodies reacting with the polypeptide of the present invention in a liquid phase, recognize different epitopes, a radioimmunoassay method using both the protein of the invention labeled with an radioisotope such as $^{125}$I and the antibody recognizing the protein of the invention, and the like.

A method of quantifying mRNA of the polypeptide of the present invention is also well-known in the art. For example, the expression level of the DNA encoding the polypeptide of the present invention can be quantified at the mRNA level by the Northern hybridization method or PCR method using the polynucleotide of the present invention or the above oligonucleotide prepared from the DNA. Such techniques are well-known in the art, and are also described in the references enumerated in this specification.

These polynucleotides can be obtained by any methods known in the art, and nucleotide sequences of these polynucleotides can be determined. For example, when a nucleotide sequence of the antibody is known, the polynucleotide encoding this antibody can be assembled from chemically synthesized oligonucleotides (as described in, for example, Kutmeier et al., BioTechniques 17:242 (1994)), and briefly, this includes synthesizing overlapping nucleotides containing the part of the sequence encoding the antibody, annealing and ligating these oligonucleotides, and amplifying the resulting ligated oligonucleotide by PCR.

The polynucleotide encoding the antibody can be prepared from a nucleic acid derived from a suitable source. A clone containing a nucleic acid encoding a certain antibody is not available, but when a sequence of its antibody molecule is known, the nucleic acid encoding the immunoglobulin can be chemically synthesized or can be obtained from a suitable source (for example, an antibody cDNA library or a cDNA library generated from any tissues or cells (for example, a hybridoma cell selected for expressing the antibody of the present invention) or a nucleic acid isolated therefrom (preferably polyA+RNA)), for example by PCR amplification with synthetic primers hybridizable with the 3'- and 5'-terminals of the sequence, in order to identify an antibody-coding cDNA clone from a cDNA library, or by cloning with an oligonucleotide probe specific to the specific gene sequence. The nucleic acid amplified by PCR can be cloned into a replicable cloning vector by methods well-known in the art.

Once the nucleotide sequence of the antibody and the corresponding amino acid sequence are determined, the nucleotide sequence of the antibody is manipulated using well-known methods for manipulation of nucleotide sequences (for example, recombinant DNA techniques, site-directed mutagenesis, PCR and the like) (see, for example, techniques described in Sambrook et al., 1990, Molecular Cloning, A Laboratory Manual, 2nd ed., Cold Spring Harbor Laboratory, Cold Spring Harbor, N.Y. and Ausubel et al. (eds.), 1998, Current Protocols in Molecular Biology, John Wiley & Sons, NY, the disclosure of which is incorporated herein by reference in their entirety)), whereby the antibody having, for example, an amino acid sequence which is so different as to generate amino acid substitution, deletion and/or insertion can be produced.

In a specific embodiment, an amino acid sequence of a heavy chain variable domain and/or a light chain variable domain can be examined by a method well-known in the art in order to identify a sequence of a complementarity determining region (CDR), for example by making comparison with known amino acid sequences of another heavy chain variable region and light chain variable region in order to identify a hypervariable region. Using routine recombinant DNA techniques, one or more CDRs can be inserted into a framework region as described above (for example, into a human framework region in order to humanize the non-human antibody). This framework region can naturally occur or can be a consensus framework region, preferably a human framework region (for the enumerated human framework regions, see e.g. Chothia et al., J. Mol. Biol. 278:457-479 (1998)). Preferably, a polynucleotide formed by combining the framework region with CDR encodes an antibody binding specifically to the polypeptide of the present invention. As discussed above, the substitution of one or more amino acids can be generated preferably in the framework region, and such substitution of amino acids preferably improves the binding of the antibody to its antigen. Such method can be used to generate the substitution or deletion of amino acid cysteine residues in one or more variable regions involved in disulfide linkages in a chain, in order to produce an antibody molecule deficient in one or more disulfide linkages. Other modifications of the polynucleotide are contained in the present invention and techniques in this field.

Techniques developed for the production of a "chimeric antibody" by splicing a gene derived from a mouse antibody molecule having suitable antigen specificity, together with a gene derived from a human antibody molecule having a suitable biological activity (Morrison et al., Proc. Natl. Acad. Sci. 81:851-855 (1984); Neuberger et al., Nature 312:604-608 (1984); Takeda et al., Nature 314:452-454 (1985)), can also be used. As described above, the chimeric antibody is a molecule whose different parts are derived from different animal species, and such a molecule (for example, humanized antibody) has variable regions derived from constant regions of mouse mAb and human immunoglobulin.

When a single-chain antibody is to be produced, known techniques described with respect to production of the single-chain antibody (U.S. Pat. No. 4,946,778; Bird, Science 242: 423-42 (1988); Huston et al., Proc. Natl. Acad. Sci. USA 85:5879-5883 (1988); and Ward et al., Nature 334:544-54 (1989)) can be utilized. The single-chain antibody is formed by allowing heavy- and light-chain fragments of Fv region to be linked with each other via an amino acid crosslinkage, thereby forming a single-chain polypeptide. Techniques for assembling functional Fv fragments in *E. coli* can also be used (Skerra et al., Science 242:1038-1041 (1988)).

(Method of Producing the Antibody)

The antibody of the present invention can be produced by chemical synthesis, or preferably by recombinant expression techniques, according to any methods known in the art for antibody synthesis.

Recombinant expression of the antibody of the present invention, a fragment thereof, a derivative thereof, or an analog thereof (for example, the heavy or light chain of the invention or the single-chain antibody of the invention), requires the construction of an expression vector containing a polynucleotide encoding the antibody. Once the polynucleotide encoding the antibody molecule of the invention, the heavy or light chain of the antibody, or a fragment thereof (preferably containing the heavy or light chain variable domain) is obtained, a vector for production of the antibody molecule can be generated by recombinant DNA techniques using techniques well-known in the art. Accordingly, the method of preparing the protein by expressing the polynucleotide containing the nucleotide sequence encoding the antibody is described in this specification. Methods well-known to those skilled in the art can be used in construction of the expression vector containing a sequence encoding the antibody, a suitable transcription regulatory signal, and a translation regulatory signal. These methods include, for example, in vitro recombinant DNA techniques, synthesis techniques and in vivo genetic recombination. Accordingly, the present invention provides a replicable vector comprising a nucleotide sequence encoding the antibody molecule of the invention, a heavy or light chain thereof, or a variable domain of the heavy or light chain, operatively linked to a promoter. Such a vector can contain a nucleotide sequence encoding a constant region of the antibody molecule (see, for example, PCT Publication WO86/05807; PCT Publication WO89/01036; and U.S. Pat. No. 5,122,464), and the variable domain of this antibody can be cloned into such vector in order to express the whole of the heavy or light chain.

The expression vector is transferred into a host cell by conventional techniques, and then this transfected cell is cultured by conventional techniques to produce the antibody of the present invention. Accordingly, the present invention encompasses a host cell comprising a polynucleotide encoding the antibody molecule of the invention, a heavy or light chain thereof, or the single-chain antibody of the invention, operatively linked to a heterogeneous promoter. In a preferable embodiment for expression of the double-chain antibody, the vector encoding both heavy and light chains can be co-expressed the whole of the immunoglobulin molecule in host cells, as will be described in detail.

In a related aspect of the invention, there is provided a pharmaceutical composition (for example, a vaccine composition) for application to prophylaxis or therapy. Such compositions generally contain the immunogenic polypeptide or polynucleotide of the present invention and an immunostimulant (for example, adjuvant).

The antibody (for example, the monoclonal antibody) of the present invention can be used to isolate the polypeptide of the present invention and the like by standard techniques (for example, affinity chromatography or immune precipitation). An antibody specific to a certain factor can facilitate purification of its natural factor from a cell or its recombinantly produced factor expressed in a host cell. Such an antibody can be used to detect the protein of the present invention (for example, in a cell lysate or a cell supernatant) to evaluate the expression level and pattern of the protein of the present invention. For example, such an antibody can be used in some procedures in a clinical test for diagnostically monitoring the level of the protein in tissues in order to determine the effectiveness of a predetermined treatment regimen. Detection can be made easy by linking (that is, physically linking) the antibody with a detectable substance. Examples of the detectable substance include various enzymes, prosthetic groups, fluorescent substances, luminescent substances, bioluminescent substances and radioactive substances. Suitable examples of enzymes include, but are not limited to, horseradish peroxidase, alkali phosphatase, β-galactosidase and acetyl choline esterase; suitable examples of the prosthetic groups include, but are not limited to, streptavidin/biotin and avidin/biotin; suitable examples of the fluorescent substances include, but are not limited to, umbelliferone, fluorescein, fluorescein isothiocyanate, rhodamine, dichlorotriazinylamine fluorescein, dansyl chloride and phycoerythrin; examples of the luminescent substances include, but are not limited to, luminol; examples of the bioluminescent substances include, but are not limited to, luciferase, luciferin and aequorin; and suitable examples of the radioactive substances include, but are not limited to, $^{125}$I, $^{131}$I, $^{35}$S and $^{3}$H.

Another aspect of the invention relates to a method of inducing an immune response to the polypeptide of the present invention in a mammal by administering, to the mammal, the polypeptide in an amount sufficient to induce the immune response The amount of the polypeptide though depending on animal species and the size of the animal can be determined by those skilled in the art.

(Screening)

In this specification, "screening" refers to selection of a target such as a living organism or a substance having a certain property of interest, from a population containing a large number of individuals by a specific operation/evaluation method. For screening, the factor (for example, the antibody), the polypeptide or the nucleic acid according to the present invention can be used. In screening, an in vitro or in vivo system of using existing substances may be used, or a library formed by using an in silico system (system using a computer) may also be used. In the present invention, it is appreciated that compounds having a desired activity obtained by screening fall under the scope of the invention. In the present invention, it is also contemplated to provide a chemical obtained by computer modeling based on the disclosure of the invention.

In an embodiment, the present invention provides an assay for screening a candidate compound or a test compound for binding to the protein of the invention, the polypeptide of the invention or a biologically active moiety thereof, or regulating the activity thereof. The test compound in the present invention is obtained by using any one of a plurality of approaches in the combinatorial library method known in the art, including: a biological library; a spatially accessible parallel solid phase or solution phase library; a synthetic library method requiring deconvolution; a "1 bead 1 compound" library method; and a synthetic library method using selection by affinity chromatography. The biological library approach is limited to the peptide library, while the other four approaches can be applied to low-molecule libraries of peptides, non-peptide oligomers or compounds (Lam (1997) Anticancer Drug Des. 12:145).

Examples of the method for synthesis of the molecule library can be found in the art, for example in the following literature: De Witt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew Chem. Int. Ed. Engl. 33:2059; Carell et al. (1994) Angew Chem. Int. Ed. Engl. 33:2061; and Callop et al. (1994) J. Med. Chem. 37:1233.

The compound library can be presented in solution (for example, Houghten (1992) BioTechniques 13:412-421), on beads (Lam (1991) Nature 354:82-84), on chips (Fodor (1993) Nature 364:555-556), microorganisms (Ladner U.S. Pat. No. 5,223,409), spores (Ladner, supra), plasmids (Cull et al. (1992) Proc. Natl. Acad. Sci. USA 89:1865-1869) or on phages (Scott & Smith (1990) Science 249:386-390; Devlin (1990) Science 249:404-406; Cwirla et al. (1990) Proc. Natl. Acad. Sci. U.S.A. 87:6378-6382; Felici (1991) J. Mol. Biol. 222:301-310; and Ladner supra).

(Pharmacological Composition)

The polynucleotide, the expression vector containing the polynucleotide, the gene-transfer vector, the antisense nucleic acid, the polypeptide and the antibody to the polypeptide according to the present invention can also be used as ingredients in a pharmaceutical composition for promoting the growth of vascular endothelial cells, for promoting transcription from c-fos promoter, for promoting transcription from VEGF promoter and for promoting angiogenesis, as well as for treatment, prevention, diagnosis or prognosis of arteriosclerosis obliterans, Buerger disease, peripheral blood vessel disease, angina, myocardial infarction, cerebral infarction, ischemic heart disease and ischemic cerebral disease.

The "effective amount" of the agents in this specification refers to the amount in which the desired effect of the agents can be exerted. In this specification, the minimum concentration amount of such an effective amount refers sometimes to the minimum effective amount. Such a minimum effective amount is well-known in the art, and the minimum effective amount of the agent has been determined usually by those skilled in the art or can be suitably determined by those skilled in the art. For determination of such effective amount, an animal model and the like can be used, in addition to actual administration. The present invention is also useful in determining such an effective amount.

In this specification, the "pharmaceutically acceptable carrier" is a substance used in producing pharmaceutical preparations or agricultural chemicals, such as animal drugs, which do not adversely affect the active ingredient. For example, such pharmaceutically acceptable carriers include, but are not limited to, an antioxidant, preservative, coloring agent, flavor, diluent, emulsifier, suspending agent, solvent, filler, bulking agent, buffer agent, delivery vehicle, excipient and/or agrochemical or pharmaceutical adjuvant.

Those skilled in the art can easily determine the type and amount of the agents used in the treatment method of the present invention, on the basis of information (for example, information on a disease) obtained by the method of the present invention and in consideration of the intended use, objective disease (type, severity and the like), the age, weight, sex and anamnesis of the patient, and the form or type of the site to which the chemical is administered. The frequency at which the monitoring method of the invention is applied to a subject (or a patient) can also be determined easily by those skilled in the art in consideration of the intended use, objective disease (type, severity and the like), the age, weight, sex and anamnesis of the patient, and the therapeutic process. The frequency of monitoring the state of disease is for example once per day to once per several months (for example, once per week to once per month). Monitoring is performed preferably once per week to once per month, while progress is observed.

If necessary, two or more chemicals can be used in the therapy of the present invention. When two or more chemicals are used, agents having similar properties or derived from the same origin, or agents having different properties or derived from different origins, may be used. Information on disease levels for the method of administering two or more agents can also be obtained by the method of the present invention.

In the present invention, those skilled in the art will easily appreciate that when analysis results of a certain sugar chain structure in living organism, cultured cells and tissues of similar types (for example, mouse and human) are correlated with disease levels, analysis results of the corresponding sugar chain structure can be correlated with disease levels. Such features are described and supported in, for example, DOUBUTSU-BAIYOU-SAIBOU MANYUARU (Animal Cultured Cell Manual) (in Japanese), edited and authored by Seno et al., Kyoritsu Shuppan Co., Ltd., 1993, the disclosure of which is expressly incorporated herein by reference in its entirety.

(Gene Therapy)

For general outlines of methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Generally known recombinant DNA techniques used in gene therapy are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

The nucleic acid construct used in gene therapy can be administered topically or systemically using a well-known gene-transfer vector. When such nucleic acid construct includes a protein-coding sequence, expression of the protein can be induced using an endogenous mammalian promoter or a heterogeneous promoter. Expression of the coding sequence can be constitutive or regulated.

When various well-known gene-transfer vectors are used as a composition for gene therapy, administration of the vector can be carried out by directly injecting a suspension of the vector in PBS (phosphate-buffered saline) or in physiological saline topically (for example, into cancer tissues, the liver, muscle and brain) or by injecting it intravascularly (for example, intra-arterially, intravenously and intraportally).

In one embodiment, the gene-transfer vector can be formulated generally by mixing it in an injectable unit dose (solution, suspension or emulsion) with a pharmaceutically acceptable carrier (which is nontoxic to a recipient in the dosage and concentration of the used agent and is compatible with other ingredients in the formulation). The formulation is preferably free of an oxidizing agent and other compounds known to be harmful to the gene-transfer vector.

The carrier suitably contains a very small amount of an additive that enhances isotonicity and chemical stability. Such substance is nontoxic to a recipient in the dosage and concentration of the agent used, and can include buffer agents such as phosphoric acid, citric acid, succinic acid, acetic acid and other organic acids or salts thereof; an antioxidant such as ascorbic acid; a low-molecular (about 9-mer or less) polypeptide (for example, polyarginine or tripeptide); a protein (for example, serum albumin, gelatin, or immunoglobulin); a hydrophilic polymer (for example, polyvinyl pyrrolidone); an amino acid (for example, glycine, glutamic acid, aspartic acid, or arginine); monosaccharide, disaccharide and other carbohydrates (including cellulose or derivatives thereof, glucose, mannose, or dextrin); a chelating agent (for example, EDTA); sugar alcohol (for example, mannitol or sorbitol); a counterion (for example, sodium); and/or a nonionic surfactant (for example, polysorbate, poloxamer), or PEG.

A pharmaceutical composition containing the gene-transfer vector can be stored typically as an aqueous solution in a unit or multi-dose vessel such as a sealed ampoule or a vial.

The pharmaceutical composition containing the gene-transfer vector is formulated and administered in a mode in accordance with GMP (good medical practice), in consideration of the clinical condition (for example, conditions to be prevented or treated) of each patient, the delivery site, target tissue, administration method and regimen of the pharmaceutical composition containing the gene-transfer vector and other factors known to those skilled in the art.

For example, when the HVJ (Sendai virus) envelope vector is administered to a human, the envelope vector is administered in an amount corresponding to 20 to 20,000 HAU, preferably 60 to 6,000 HAU, more preferably 200 to 2,000 HAU per mouse. The amount of the exogenous gene contained in the envelope vector is 0.1 to 100 µg, preferably 0.3 to 30 µg, more preferably 1 to 10 µg, per mouse.

When the HVJ (Sendai virus) envelope vector is administered to a human, the envelope vector is administered in an amount corresponding to 400 to 400,000 HAU, preferably 1,200 to 120,000 HAU, more preferably 4,000 to 40,000 HAU per subject. The amount of the exogenous gene contained in the envelope vector is 2 to 2,000 µg, preferably 6 to 600 µg, more preferably 20 to 200 µg, per subject.

The polypeptide of the present invention can be introduced into the gene-transfer vector in the same manner as used in the above gene therapy and the polypeptide can be delivered to a desired site.

When the polypeptide or polynucleotide of the present invention is used in the treatment of disease, for example, a method of directly injecting it into the skeletal muscle or heart muscle or a transfer method comprising encapsulating it in a vector, can be used. In the case of the polynucleotide, targeting by direct injection or intravascular administration of a virus vector (adenovirus vector, adeno-associated virus vector and the like) or a non-virus vector (liposome, HVJ-E and the like) is feasible. In the case of the polypeptide, HVJ-E is preferable, and direct administration is considered effective. There is also a method of sustained release by encapsulating it in gelatin hydrogel, atelo-collagen, or polylactic acid and then embedding it near an ischemic site (in the muscle, or brain, or subcutaneously).

By such a method, the growth and migration of vascular endothelial cells is promoted, and blood vessels are newly formed through tube formation. By migration of vascular smooth muscle cells, the blood vessels are reinforced and become functional blood vessels through which blood can be supplied peripherally. Collateral blood flow is thereby formed around an occlusive site of a blood vessel, to increase the amount of blood circulating to the ischemic site, thus enabling treatment of peripheral blood vessel disease, ischemic heart, and cerebral disease.

Gene therapy using VEGF is reported in Isner, J., et al., Clinical evidence of angiogenesis after arterial gene transfer of phVEGF165 in a patient with an ischemic limb. The Lancet 348, 370-374, (1996); Baumgartner, L., et al., Constitutive expression of phVEGF165 after intramuscular gene transfer promotes collateral vessel development in patients with clinical limb ischemia. Circulation, 97, 1114-1123, (1998); and Machens, H-G., et al., Angiogenic effects of injected VEGF165 and sVEGFR-1 in a rat flap model. J. Surgical Research 111, 136-142, (2003).

Angiogenic peptides are reported in Li, J., et al.: pR39, a peptide regulator of angiogenesis. Nature Medicine 6, 49-55, (2000) and Koczulla, R., et al.: An angiogenic role for the human peptide antibiotic LL-37/hCAP-18. J. Clin. Invest. 111, 1665-1672, (2003).

Animal models are reported in Couffinhal, T., et al.: Mouse model of angiogenesis. Am. J. Pathol. 152, 1667-1679, (1998).

Angiogenesis can also be detected by ligating and removing one of femoral arteries of a mouse, a rat or a rabbit thereby forming an ischemic site, then intramuscularly administering the gene or protein, and evaluating its therapeutic effect in terms of the number of blood vessels by staining of tissues or the blood stream using a laser doppler, or by angiography.

(General Techniques Used in this Specification)

Unless otherwise specified, the techniques used in the present invention make use of well-known routine techniques within the repertoire of those skilled in the art of sugar chain science, microfluidics, microfabrication, organic chemistry, biochemistry, genetic engineering, molecular biology, microbiology, genetics and related fields. Such techniques are sufficiently described in, for example, the literature listed below, and literature cited in other parts of this specification.

Microfabrication is described in, for example, Campbell, S. A. (1996). The Science and Engineering of Microelectronic Fabrication, Oxford University Press; Zaut, P. V. (1996). Micromicroarray Fabrication: a Practical Guide to Semiconductor Processing, Semiconductor Services; Madou, M. J. (1997). Fundamentals of Microfabrication, CRC1 5 Press; Rai-Choudhury, P. (1997). Handbook of Microlithography, Micromachining, & Microfabrication: Microlithography, the relevant part of which is expressly incorporated herein by reference.

The molecular biological techniques, biochemical techniques, microbiological techniques and sugar-chain scientific techniques used in this specification are well-known and used in the art and described in, for example, Maniatis, T. et al. (1989). Molecular Cloning: A Laboratory Manual, Cold Spring Harbor and 3rd Ed. (2001); Ausubel, F. M., et al. eds, Current Protocols in Molecular Biology, John Wiley & Sons Inc., NY, 10158 (2000); Innis, M. A. (1990). PCR Protocols: A Guide to Methods and Applications, Academic Press; Innis, M. A. et al. (1995). PCR Strategies, Academic Press; Sninsky, J. J. et al. (1999). PCR Applications: Protocols for Functional Genomics, Academic Press; Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press; Method in Enzymology 230, 242, 247, Academic Press, 1994; and ZIKKEN IGAKU (Experimental Medicine) "IDENSHI-DOUNYU & HATSU-GEN-KAISEKI ZIKKEN-HOU (Experimental Methods of Gene Introduction & Expression Analysis)", Separate Volume, published by Yodosha Co., Ltd., 1997, the disclosure (only relevant parts or the entirety) of which is expressly incorporated herein by reference.

(Formulation)

The present invention also provides a method of treatment and/or prevention of diseases or disorders (for example, infections), by administering an effective amount of the therapeutic agent to a subject. The therapeutic agent refers to the composition of the present invention combined with a pharmaceutically acceptable carrier (for example, a sterilized carrier).

The therapeutic agent is formulated and administered in compliance with GMP (good medical practice), in consideration of clinical conditions (particularly side effects upon treatment with only the therapeutic agent) of each patient, a delivery site, an administration method, a regimen and other factors known to those skilled in the art. Accordingly, the "effective amount" of interest in this specification is determined by such consideration.

Generally, the total pharmaceutical effective amount of the therapeutic agent parenterally administered per dose is in the range of about 1 µg/kg (patient weight)/day to 10 mg/kg/day, but the dose may change from a therapeutic viewpoint. The dose of the cellularly biologically active substance of the present invention is at least 0.01 mg/kg/day, most preferably in the range of about 0.01 mg/kg/day to about 1 mg/kg/day for human. When the therapeutic agent is to be successively administered, it is administered typically at an administration rate of about 1 µg/kg/hour to about 50 µg/kg/hour either by injecting it once to 4 times per day or by continuous subcutaneous injection (for example with a mini-pump). A bag solution for intravenous administration can also be used. The treatment period necessary for observing a change and the period of from the treatment to the occurrence of response appears to change depending on the desired effect.

The therapeutic agent can be administered orally, intrarectally, parenterally, intracisternally, intravaginally, intraperitoneally, topically (using a powder, ointment, gel, eye-drop or transdermal patch) or to the mouth, or as an oral or nasal spray. The "pharmaceutically acceptable carrier" refers to a nontoxic solid, semisolid or liquid excipient, diluent, encapsulating material or an adjunct for formulation in any form. The term "parenteral" as used this specification refers to a mode of administration involving intravenous, intramuscular, intraperitoneal, intrasternal, subcutaneous and intra-articular injection or infusion.

The therapeutic agent of the present invention can be suitably administered by a sustained release system. The therapeutic agent can be administered for example as a sustained-release therapeutic agent orally, intrarectally, parenterally, intracisternally, intravaginally, intraperitoneally, topically (using a powder, ointment, gel, eye-drop or transdermal patch) to the mouth, or as an oral or nasal spray. The "pharmaceutically acceptable carrier" refers to a nontoxic solid, semisolid or liquid excipient, diluent, encapsulating material or an adjunct for formulation in any form. The term "parenteral" as used this specification refers to a mode of administration involving intravenous, intramuscular, intraperitoneal, intrasternal, subcutaneous and intra-articular injection.

The therapeutic agent of the present invention can be suitably administered by a sustained release system. Preferable examples of the sustained-release therapeutic agent include suitable polymer substances (for example, a semi-permeable polymer matrix in the form of a molded product (for example, a film or microcapsule), suitable hydrophobic substances (for example, as an emulsion in an oil of acceptable qualities), or ion-exchange resin and sparingly soluble derivatives (for example, sparingly soluble salts).

The sustained-release matrix includes polylactide (U.S. Pat. No. 3,773,919, EP58,481), an L-glutamic acid/γ-ethyl-L-glutamate copolymer (Sidman et al., Biopolymers 22:547-556 (1983)), poly(2-hydroxyethyl methacrylate) (Langer et al., J. Biomed. Mater. Res. 15:167-277 (1981)), and Langer, Chem. Tech. 12:98-105 (1982)), ethylene vinyl acetate (Langer et al., ibidem) and poly-D-(−)-3-hydroxybutyric acid (EP133,988).

The sustained-release therapeutic agent also includes the therapeutic agent of the invention encapsulated in a liposome (see Langer, Science 249:1527-1533 (1990); Treat et al., Liposomes in the Therapy of Infectious Disease and Cancer, edited by Lopenz-Berestein and Fidler, Liss, New York, pp. 317-327 and pp. 353-365 (1989)). The therapeutic agent-containing liposome can be prepared by methods known per se: DE3,218,121; Epstein et al., Proc. Natl. Acad. Sci. USA 82:3688-3692 (1985); Hwang et al., Proc. Natl. Acad. Sci. USA 77:4030-4034 (1980); EP52,322; EP36,676; EP88,046; EP143,949; EP142,641; Japanese Patent Application No. 83-118008; U.S. Pat. Nos. 4,485,045 and 4,544,545; and EP No. 102,324. Usually, the liposome is in a small (about 200 to 800 Å) unilamellar form, having a lipid content higher than about 30 mol % cholesterol, wherein the ratio is selected and optimized for the optimum therapeutic agent.

In a further embodiment, the therapeutic agent of the present invention is delivered with a pump (see Langer, supra; Sefton, CRC Crit. Ref. Biomed. Eng. 14:201 (1987); Buchwald et al., Surgery 88:507 (1980); and Saudek et al., N. Engl. J. Med. 321:574 (1989).

Another regulated release system has been discussed in a review article by Langer (Science 249:1527-1533 (1990)).

For parenteral administration, in one embodiment, the therapeutic agent is generally formulated in an injectable form of unit dosage (solution, suspension or emulsion) by mixing it at a desired purity with a pharmaceutically acceptable carrier which is nontoxic to a recipient at the dosage and concentration of the used agent and is compatible with other ingredients in the formulation. The formulation is preferably free of an oxidizing agent and other compounds known to be harmful to the therapeutic agent.

Generally, the therapeutic agent is contacted uniformly and closely with a liquid carrier or a finely divided solid carrier to prepare a formulation. If necessary, the product is then formed into a desired formulation. The carrier is preferably a parenteral carrier, more preferably a solution isotonic to blood of a recipient. Examples of such carrier vehicle include water, physiological saline, Ringer's solution and dextrose solution. Similar to liposomes, non-aqueous vehicles such as nonvolatile oil and ethyl oleate are also useful in this specification.

The carrier suitably contains a very small amount of an additive enhancing isotonicity and chemical stability. Such a substance is nontoxic to a recipient at the dosage and concentration of the agent used, and can include buffer agents such as phosphate, citrate, succinate, acetic acid, and other organic acids or salts thereof; an antioxidant such as ascorbic acid; a low-molecular weight (about 9-mer or less) polypeptide (for example, polyarginine or tripeptide); a protein such as serum albumin, gelatin, or immunoglobulin; a hydrophobic polymer such as polyvinyl pyrrolidone; an amino acid such as glycine, glutamic acid, aspartic acid or arginine; monosaccharide, disaccharide and other carbohydrates, including cellulose or derivatives thereof, glucose, mannose, or dextrin; a chelating agent such as EDTA; sugar alcohol such as mannitol or sorbitol; a counterion such as sodium; and/or a nonionic surfactant such as polysorbate, poloxamer or PEG.

The therapeutic agent is formulated typically at a concentration of about 0.1 mg/ml to 100 mg/ml, preferably 1 to 10 mg/ml in such vehicles at pH value of about 3 to 8. It is appreciated that a salt is formed using the specific excipient, carrier or stabilizer described above.

Any agents used in therapeutic administration can be in a sterile state, that is, in a state free from a living organism and virus, other than the virus serving as the active ingredient. The sterile state can be easily attained by filtration through a sterile filtration membrane (for example, 0.2 micron membrane). Generally, the therapeutic agent is arranged in a vessel having a sterile access port, for example in a vial or a solution bag for intravenous administration, equipped with a stopper and being capable of being pricked with a hypodermic needle.

The therapeutic agent is stored usually as an aqueous solution or a lyophilized product for reconstitution, in a unit-dose or multi-dose vessel, for example in a sealed ampoule or a vial. The lyophilized product is produced for example by loading a 10-ml vial with 5 ml of 1% (w/v) sterilely filtered aqueous solution of the therapeutic agent and then lyophilizing the mixture. The lyophilized therapeutic agent is reconstituted with distilled water for injection, to prepare an injection solution.

The present invention also provides a pharmaceutical pack or kit provided with one or more vessels filled with one or more components of the therapeutic agent of the present invention. A notice in form stipulated by government organizations regulating production, use or sale of pharmaceutical preparations or biological products, can be attached to such a vessel, and this notice indicates the approval of the government organizations of the production, use or sale of such, for administration to humans. The therapeutic agent can be used in combination with another therapeutic compound.

The therapeutic agent of the present invention can be administered solely or in combination with another therapeutic agent. For example, the therapeutic agent and another therapeutic agent can be administered all at once as a mixture; simultaneously or in parallel but separately; or with time or at intervals. This indicates that the agents combined with each other are administered together as a therapeutic mixture, and/ or involves the procedure in which the agents combined with each other are administered separately but simultaneously, for example, thorough separate venous lines to the same individual. The administration thereof "in combination" further encompasses separate administration of one compound or agent given firstly and secondly.

In a specific embodiment, the pharmaceutical composition of the present invention is administered in combination with an anticancer agent.

In a further embodiment, the therapeutic agent of the present invention is administered in combination with another therapeutic regimen or prophylactic regimen (for example, radiotherapy).

Hereinafter, the present invention is described in more detail by reference to the Examples, but the present invention is not limited thereto.

EXAMPLES

Example 1

Preparation and Use of a Gene-Transfer Vector Having an Exogenous Gene Encapsulated in a Component Containing a Virus Envelope-Derived Protein (Preparation of Virus)

HVJ, Z strain was purified by differential centrifugation as previously described, above (Kaneda, Cell Biology: A Laboratory Handbook, J. E. Celis (Ed.), Academic Press, Orlando, Fla., vol. 3, pp. 50-57 (1994)). The purified HVJ was resuspended in a buffered saline solution (BSS: 137 mM NaCl, 5.4 mM KCl, 10mM Tris-HCl, pH 7.5) and its virus titer determined by measuring absorbance at 540 nm. The optical density at 540 nm corresponds to 15,000 hemagglutinating unit (HAU) and is correlated with fusion activity.

(Preparation of a Gene-Transfer Vector)

A lipid mixture of 3.56 mg phosphatidylcholine and 0.44 mg cholesterol was dissolved in chloroform, and this lipid solution was evaporated in a rotary evaporator (Uchida et al., J. Cell. Biol. 80:10-20 (1979)). The dried lipid mixture was dissolved completely by Vortex in a protein solution (1.6 mg) of 2.0 ml flow-through fraction containing 0.85% NP-40. Then, this solution was dialyzed against 10 mM phosphate buffer (pH 7.2) containing 0.3 M sucrose and 1 mM KCl to remove NP-40. The dialysis was carried out for 6 days while the buffer was exchanged everyday. This dialyzed solution was applied onto agarose beads (Bio-Gel A-50m) (Bio-Rad Laboratories, Hercules, Calif., USA) equilibrated with 10 mM phosphate buffer (pH 5.2) containing 0.3 M sucrose and 1 mM KCl. Fractions having an optical density of higher than 1.5 at 540 nm were collected as re-constituted fusion particles and then fused with liposomes charged with nucleic acid, prepared from 10 mg lipid as described below, to prepare a gene-transfer vector.

(Expression of Luciferase Gene in Transfected Cells Derived From Human HEK293 Strain)

To confirm the ability of the above-prepared gene-transfer vector to introduce the gene, human HEK293 strain and a luciferase gene were used as follows.

pCMV-luciferase (7.4 kb) was constructed by cloning a luciferase gene from pGEM-luc (Promega Corp., Madison, Wis., USA) at HindIII and BamHI sites into pcDNA3 (5.4 kb) (Invitrogen, San Diego, Calif., USA). A gene-transfer vector containing about 40 µg pCMV-luciferase was constructed as described above, and 1/10 (100 µl) of this gene-transfer vector (about $1.5 \times 10^{11}$ particles/ml, DNA concentration of about 40 µg/ml) was incubated with $2 \times 10^5$ cells derived from human 293 cell strain (human embryonic kidney (HEK)). Using HVJ liposomes, the same amount of luciferase DNA was introduced into $2 \times 10^5$ HEK293 cells. 24 hours after introduction, the cells were recovered, and as described in the literature (Saeki et al., Hum. Gene Ther., 8:1965-1972 (1997)), the luciferase activity assay was confirmed.

Example 2

Preparation and Use of an Inactivated HVJ Envelope Vector Utilizing a Detergent (1: Growth of HVJ)

In general, HVJ grown by inoculating a fertilized chicken egg with the seed virus may be used. However, HVJ grown by utilizing cultured cells (e.g., simian or human), or a persistent infection system (i.e., a culture solution to which a hydrolase such as trypsin is added to cultured tissue), or HVJ grown by infecting cultured cells with cloned virus genome to cause persistent infection, are applicable.

In the present example, the growth of HVJ was carried out as follows.

HVJ seed virus was grown by utilizing a SPF (Specific Pathogen Free) fertilized egg. The isolated and purified HVJ (Z species) was dispensed into a tube for storing cells, and stored in liquid nitrogen with 10% DMSO added thereto. Thus, HVJ was prepared.

Chicken eggs immediately after fertilization were obtained, and placed in an incubator (SHOWA-FURANKI P-03 type; capable of accommodating about 300 chicken eggs), and incubated for 10 to 14 days under the conditions of 36.5° C. and 40% or more humidity. In a darkroom, the viability of the embryo, as well as the presence of an air chamber and a chorioallantois were confirmed using an egg tester (one in which light from a light bulb is projected through a window having a diameter of about 1.5 cm). A virus-injection site was marked in pencil about 5 mm above the chorioallantois (the position was selected so as avoid any thick blood vessels). The seed virus (which was taken out of the liquid nitrogen) was diluted by 500 times with a polypeptone solution (to which 1% polypeptone, 0.2% NaCl was mixed, and which was prepared so as to have pH 7.2 with 1 M NaOH, then autoclave-sterilized, and stored at 4° C.), and left at 4° C. The egg was disinfected with Isodine™ and alcohol. A small hole was made in the virus-injection site with a pick. Using a needled 1 ml syringe (26 gauge), 0.1 ml of the diluted seed virus was injected into the chorioallantoic cavity. Molten paraffin (melting point: 50 to 52° C.) was placed on the hole using a Pasteur pipette to close the hole. The egg was placed in an incubator and bred for three days under the conditions of 36.5° C. and 40% or more humidity. Then, the inoculated egg was left overnight at 4° C. On the following day, the air chamber portion of the egg was broken with a tweezer, and a 10 ml syringe with an 18 gauge needle was placed in the chorioallantois so as to suction off the chorioallantoic fluid, which was collected in a sterilized bottle and stored at 4° C.

(2: Purification of HVJ)

HVJ may be purified by a purification method utilizing centrifugation, a purification method utilizing a column, or any other purification methods known in the art.

(2.1: Purification Method Using Centrifugation)

In short, a solution containing mature viruses was collected, and the solution centrifuged at low speed to remove the tissue or cell debris in the culture solution and the chorioallantoic fluid. A supernatant thereof was purified by high-speed centrifugation (27,500×g, 30 minutes) and ultra centrifugation (62,800×g, 90 minutes) utilizing a sucrose density gradient (30 to 60% w/v). Care should be taken to treat the virus as gently as possible during purification, and to store the virus at 4° C.

Specifically, in the present example, HVJ was purified using the following method.

About 100 ml of HVJ-containing chorioallantoic fluid (the chorioallantoic fluid from a chicken egg containing HVJ, which was collected and stored at 4° C.) was placed in two 50 ml centrifuge tubes with a wide-mouth Komagome type pipette (see Saeki, Y., and Kaneda, Y: Protein modified liposomes (HVJ-liposomes) for the delivery of genes, oligonucleotides and proteins. Cell Biology; A laboratory handbook (2nd edition) ed. by J. E. Celis (Academic Press Inc., San Diego) vol. 4, 127 to 135,1998), centrifuged in a low-speed centrifuge at 3000 rpm, at 4° C. for 10 minutes (without braking). Thus, the tissue debris from the egg was removed.

After centrifugation, the supernatant was dispensed into four 35 ml centrifuge tubes (designed for high-speed centrifugation), and centrifuged for 30 minutes in a fixed-angle rotor at 27,000 g, (with acceleration and braking). The supernatant was removed, BSS (10 mM Tris-HCl (pH 7.5), 137 mM NaCl, 5.4 mM KCl; autoclaved and stored at 4° C.) (BSS may be replaced by PBS) was added to the precipitate in an amount of about 5 ml per tube, and allowed to stand overnight at 4° C. While gently pipetting with a wide-mouth Komagome type pipette, the precipitate was isolated and collected in one tube, and was similarly centrifuged for 30 minutes in a fixed-angle rotor at 27,000g. The supernatant was removed, and about 10 ml of BSS was added to the precipitate, and the precipitate was allowed to stand overnight at 4° C. While gently pipetting with a wide-mouth Komagome type pipette, the precipitate was isolated, and centrifuged for 10 minutes in a low-speed centrifuge at 3000 rpm at 4° C. (without braking), thereby removing the tissue debris and agglutination masses of virus which had not been completely removed. The supernatant was placed in a fresh sterilized tube, and stored at 4° C. as the purified virus.

To 0.1 ml of this virus solution, 0.9 ml of BSS was added, and the absorption at 540 nm was measured with a spectrophotometer. The virus titer was converted into an erythrocyte agglutination activity (HAU). An absorption value of 1 at 540 nm approximately corresponded to 15,000 HAU. It is considered that HAU is substantially proportionate to fusion activity. Alternatively, the erythrocyte agglutination activity may be measured by actually using a solution containing chicken erythrocytes (0.5%), (see DOUBUTSU SAIBO RIYO JITSUYOKA MANUAL (or "Practice Manual for Using Animal Cells"), REALIZE INC. (ed. by Uchida, Oishi, Furusawa) pp. 259 to 268, 1984).

Furthermore, purification of HVJ using a sucrose density gradient may be performed as necessary. Specifically, a virus suspension is placed at the top of a centrifuge tube in which 60% and 30% sucrose solutions (autoclave-sterilized) were layered, and a density gradient centrifugation is performed for 120 minutes at 62,800×g. After centrifugation, a band which is observed in the 60% sucrose solution layer is recovered. The recovered virus suspension is dialyzed overnight at 4° C. against an external solution of BSS or PBS, thereby removing the sucrose. In the case where the virus suspension is not to be immediately used, glycerol (autoclave-sterilized) and a 0.5 M EDTA solution (autoclave-sterilized) are added to the virus suspension so as to attain final concentrations of 10% and 2 to 10 mM, respectively, and gently frozen at −80° C., before finally being stored in liquid nitrogen (frozen storage can be achieved with 10 mM DMSO, instead of glycerol and a 0.5 M EDTA solution).

(2.2: Purification Method Utilizing Columns and Ultrafiltration)

Instead of the purification method through centrifugation, purification of HVJ utilizing columns is also applicable to the present invention.

Briefly, concentration (about 10 times) via ultrafiltration utilizing a filter having a molecular weight cut-off of 50,000, and elution via ion exchange chromatography (0.3 M to 1 M NaCl), were performed to achieve purification.

Specifically, in the present example, the following method was used to purify HVJ using columns.

After chorioallantoic fluid was collected, the chorioallantoic fluid was filtrated through a membrane filter (80 μm to 10 μm). To the chorioallantoic fluid, 0.006 to 0.008% BPL (final concentration) was added (4° C., 1 hour), so as to inactivate HVJ. The chorioallantoic fluid was incubated for 2 hours at 37° C., thereby inactivating BPL.

By a tangential flow ultrafiltration method using 500KMWCO (A/G Technology, Needham, Mass.), about 10 times virus concentration was achieved. As a buffer, 50 mM NaCl, 1 mM $MgCl_2$, 2% mannitol, and 20 mM Tris (pH 7.5) were used. An HAU assay indicated an HVJ yield of approximately 100%. Thus, excellent results were obtained.

By a column chromatography method (buffer: 20 mM Tris HCl (pH 7.5), 0.2 to 1 M NaCl) using Q Sepharose FF (Amersham Pharmacia Biotech KK, Tokyo), HVJ was purified. The yield was 40 to 50%, and the purity was 99% or more.

An HVJ fraction was concentrated by a tangential flow ultrafiltration method using 500KMWCO (A/G Technology).

(3: Inactivation of HVJ)

In the case where it was necessary to inactivate HVJ, this was performed by UV light irradiation or by using an alkylating agent treatment, as described below.

(3.1: UV Light Irradiation Method)

One milliliter of HVJ suspension was placed in a dish having a diameter of 30 mm, and subjected to irradiation at 99 or 198 $mJ/cm^2$. Although gamma-ray irradiation is also applicable (5 to 20 Gy), it does not provide complete inactivation.

(3.2: Treatment Using an Alkylating Agent)

Immediately before use, 0.01% β-propiolactone was prepared in 10 mM $KH_2PO$. The solution was kept at a low temperature during preparation, and the operation was quickly performed.

To the HVJ suspension obtained immediately after purification, β-propiolactone was added to a final concentration of 0.01%, and the solution incubated on ice for 60 minutes. Thereafter, the mixture was incubated at 37° C. for 2 hours. The mixture was dispensed into Eppendorf tubes at an amount of 10,000 HAU per tube, and centrifuged for 15 minutes at 15,000 rpm. The precipitate was stored at −20° C. Instead of using the aforementioned inactivation method, without storing the precipitate at −20° C., DNA may be allowed to be incorporated through a detergent treatment to construct a vector.

(4: Construction of an HVJ Envelope Vector)

To the HVJ which had been stored, 92 μl of a solution containing 200 to 800 μg of exogenous DNA was added, and thoroughly suspended by pipetting. This solution can be stored at −20° C. for at least 3 months. By adding protamine sulfate to the DNA before mixing with HVJ, the expression efficiency was enhanced twofold or more.

This mixture was placed on ice for 1 minute, and 8 μl of octylglucoside (10%) was added. The tube was shaken on ice for 15 seconds, and allowed to standstill on ice for 45 seconds. The treatment time with the detergent is preferably 1 to 5 minutes. Instead of octylglucoside, detergents such as Triton-X100 (t-octylphenoxypolyethoxyethanol), CHAPS (3-[(3-cholamidopropyl)-dimethylammonio]-1-propane sulfonate), or NP-40 (nonylphenoxy polyethoxy ethanol) may also be used. The final concentrations of Triton-X100, NP-40, and CHAPS are preferably 0.24 to 0.80%, 0.04 to 0.12%, and 1.2 to 2.0%, respectively.

One milliliter of cold BSS was added, and the solution was immediately centrifuged for 15 minutes at 15,000 rpm. To the resultant precipitate, 300 μl of PBS or saline, etc., was added, and suspended by vortex or pipetting. The suspension may be directly used for gene transfer or may be used for gene transfer after storage at −20° C. After being stored for at least 2 months, this HVJ envelope vector maintained the same level of gene transfer efficiency.

(5: Gene Transfer to Cells Via an HVJ Envelope Vector)

(1: Gene Transfer Method)

An amount equivalent to 1,000 HAU was placed into an Eppendorf tube (30 μl), and 5 μl of protamine sulfate (1 mg/ml) was added. The medium for BHK-21 cells (which were sown in 6 wells at a density of 200,000 cells per well on the previous day) was exchanged, and 0.5 ml of medium (10% FCS-DMEM) was added per well. To each well, a mixture of the aforementioned vector (equivalent to 1,000 HAU) and protamine sulfate was added, and the plate was shaken back and forth and from right to left, whereby the vector and cells were well mixed. The mixture was left in a 5% $CO_2$ incubator for 10 minutes at 37° C.

The medium was exchanged, and the cells left overnight (16 hrs to 24 hrs) at 37° C. in a 5% $CO_2$ incubator, after which the gene expression was examined. As for luciferase (pcLuci: a luciferase gene having a CMV promoter), the cells were lysed with 0.5 ml of Cell Lysis Buffer (Promega), and the activity in 20 μl of the solution was measured using a luciferase assay kit (Promega). As for green fluorescence protein (pCMV-GFPE; Promega), the cells were observed under fluorescence microscopy in their intact form, and 5 to 8 fields were observed at a magnification rate of 400, and the ratio of cells which generated fluorescence was calculated.

Example 3

Isolation and Analysis of Gene Clone p3743 Encoding a Vascular Endothelial Growth Factor From a Human Heart cDNA Library Using the present invention, the gene of interest having desired functional properties can be separated. One embodiment of the isolation methods used is schematically shown in FIG. 1.

By actually using the gene-transfer vector prepared in Example 2 in this specification, the gene encoding the vascular endothelial growth factor was isolated. As the method of isolating the gene illustrated in the Examples, it is possible to use not only the gene-transfer vector prepared in Example 2 in this specification but also any "virus envelope vector" and "liposome vector".

A human heart cDNA library (a plasmid having human heart-derived cDNA ligated to plasmid pSPORT having a CMV promoter; GIBCO BRL) was introduced into *E. coli* DH12S, and the plasmid prepared from the *E. coli*. 200 μg of the plasmid was encapsulated in 10000 HAU of the HVJ-E gene-transfer vector (the gene-transfer vector, $3 \times 10^9$ particles, prepared in Example 2 in the present invention). As host cells, human aortic endothelial cells HEAC (Sanko Junyaku Co., Ltd.), about 5000 cells, were added together with medium to each well of a 96-well microtiter plate, then cultured overnight and used. 1/100 of the HVJ-E was added to each well containing the host cells, and then left at 37° C. for 30 minutes, followed by exchanging the medium.

The medium used is provides low-nutrition state, with a serum at a concentration of 1%, under which the cells were cultured for 1 week. Under this condition, the growth of HEAC could not be confirmed.

After 2 weeks, a cell proliferation assay was carried out. Using Cell Titer 96 (Promega) as a reagent, the oxidoreduction of mitochondria was measured as a change in the color of the reagent and used as an indicator of cell growth.

A well having the deepest color is a well in which the cells having grown most vigorously are present. Hence, the whole of the microtiterplate was read with a plate reader, and growth of the cells was shown graphically using a computer. From the cells in 2 wells showing the highest proliferation activity in the graph, a nucleic acid was prepared by using DNeasy Tissue Kit available commercially from Qiagen. Because the prepared nucleic acid contains plasmid DNA, it was introduced into competent $E.\ coli$ (DH5α, Takara Shuzo Co., Ltd.) using a heat-shock method.

This $E.\ coli$ was inoculated onto an ampicillin-containing solid-media plates to form colonies. About 20 to 200 colonies could be obtained from the DNA prepared in one well. Plasmid DNA (pDNA) was extracted from each colony and treated with restriction enzymes, thereby confirming the presence of a gene fragment in the plasmid. As a result, about 60 to 70% of the prepared plasmids were plasmids having the insert.

Then, the plasmid DNA was purified by using Endo Free Plasmid Maxi Kit from Qiagen, and the purified plasmid was encapsulated in HVJ-E and introduced again into HAEC cells, and the same cell growth experiment was carried out. In this cell growth experiment, the plasmid exhibiting significantly high cell growth is a candidate plasmid expected to contain the nucleic acid encoding the vascular endothelial growth factor.

Figure 2:
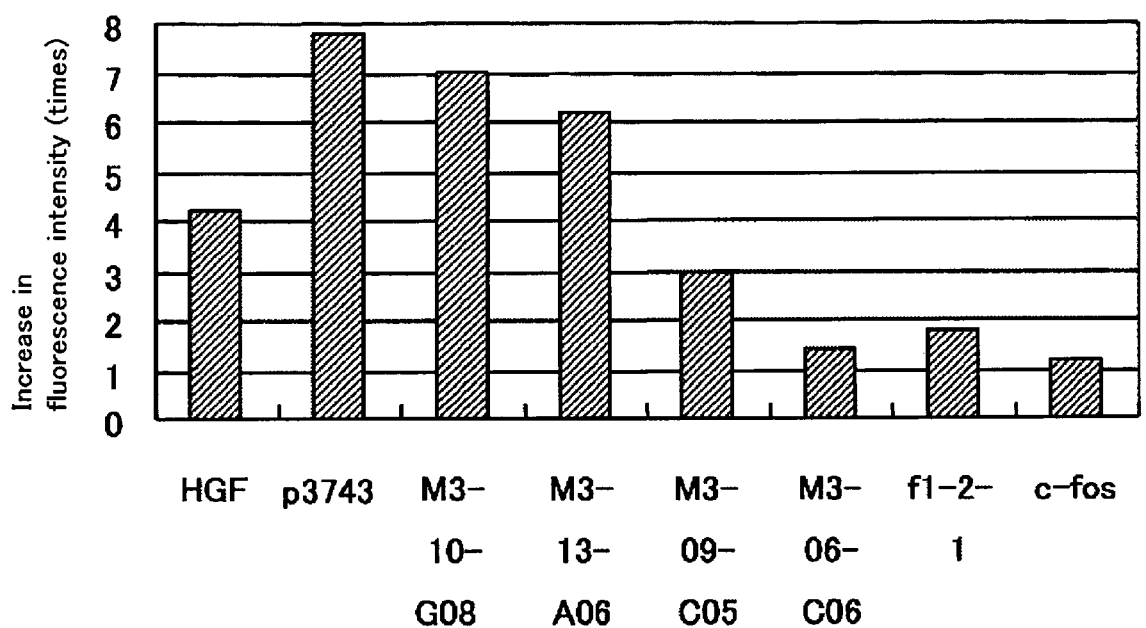
FIG. 2 is a graph showing the results of a c-fos promoter assay for the nucleic acid isolated in the present invention.

Each of nine clones having the insert was encapsulated respectively in HVJ-E and subjected to a second screening, and as a result, a gene showing a high proliferation activity was obtained. Two Additional genes were obtained, and the 3 genes in total showed a very high HAEC proliferation ability. When these 3 genes were examined two further times, the HAEC proliferation ability was confirmed. To further confirm the proliferation ability, an assay using a promoter of proto-oncogene c-fos, which is activated in the earliest stage of cell proliferation, was carried out. The gene c-fos-Luci having luciferase ligated under this promoter, and a candidate gene, were introduced in a weight ratio of 1:1 by lipofection into bovine vascular endothelial cells, and after 24 to 48 hours, the luciferase activity was measured. Plasmid c-fos-Luci is a plasmid containing 2 copies of 5'-regulatory enhancer region (−357 to −276) of c-fos, a promoter (−200 to 70) of the herpes simplex virus thymidine kinase gene, and the luciferase gene (Arterioscler Thromb Vasc Biol. 2002: 22: 238-242). As shown in FIG. 2, three genes (p3743, M3-10-G08, M3-13-A06) have a higher luciferase activity than HGF, thus indicating the potent activation of c-fos promoter by these gene products. p3743 exhibiting the highest activity among these genes was examined as described above by a promoter assay using a luciferase gene having VEGF promoter ligated thereto, to indicate the higher activation of the VEGF promoter than by VEGF as shown in the right graph in FIG. 3. That is, this result indicated the possibility of angiogenesis due to enhancement of secretion of VEGF by the gene product and activation of the known angiogenesis gene. As shown in the left graph in FIG. 3, p3743 had a higher ability to activate the c-fos promoter than VEGF. Then, when the ability of p3743 to proliferate cells was examined using human aortic endothelial cells (HAEC) and human vascular smooth muscle cell (VSMC), it was revealed that when HAEC was used as the host cell as shown in FIG. 4, the isolated nucleic acid had a higher proliferation ability than HGF. However, when human vascular smooth muscle cells were used, the activity was the same as that of the negative control, GFP.

(1. Angiogenesis Activity)

Using a Kurabo Angiogenesis kit (KZ-1000, Kurabo Industries Ltd.), tube formation was examined. A blank, vascular endothelial growth factor-A protein (VEGF-A), pVEGF plasmid (plasmid containing a gene encoding vascular endothelial growth factor), and pSPORT1 (a plasmid not containing a gene encoding vascular endothelial growth factor) were used as controls.

10 ng/ml VEGF-E (NZ-7) was added to an angiogenesis medium (KZ-1400, Kurabo Industries Ltd.), and anti-human VEGF-A neutralizing antibody was further added thereto at concentrations of 0, 250, 500 and 1000 ng/ml, respectively, and used to culture the cells.

Anti-VEGF, Human, Mouse-Mono (26503.111) (Catalog No. MAB293, manufactured by R&D) was used as anti-human VEGF-A neutralizing antibody. Culture was carried out at 37° C. in a 5% $CO_2$ incubator. The medium was exchanged on the 4th, 7th and 9th days of culture with a fresh medium containing the same additives. On the 11th day of culture, the medium was removed, and using a tube staining kit (KZ-1225 for CD31 antibody staining, Kurabo Industries Ltd.), staining was carried out according to the following procedure.

CD31 (PECAM-1) staining primary antibody (mouse anti-human CD31 antibody) was diluted 4,000-fold with a blocking solution (Dulbecco's phosphate buffer solution (PBS(−)) containing 1% BSA). 0.5 ml of this primary antibody solution was added to each well and incubated for 60 minutes at 37° C. After incubation was finished, each well was washed 3 times with 1 ml blocking solution.

Then, 0.5 ml of a secondary antibody (goat anti-mouse IgG/alkali phosphatase conjugate) solution, diluted 500-fold with the blocking solution, was added to each well and incubated for 60 minutes at 37° C., and each well was washed 3 times with 1 ml distilled water. Separately, 2 tablets of BCIP/NBT were dissolved in 20 ml distilled water and filtered through a filter with a pore size of 0.2 μm, to prepare a substrate solution. 0.5 ml of the prepared BCIP/NBT substrate solution was added to each well and incubated at 37° C. until the tube turned deep violet (usually in 5 to 10 minutes). After incubation was finished, each well was washed 3 times with 1 ml distilled water, followed by removing the washing solution using suction, and the plate was left to air-dry. After drying, each well was observed under a microscope.

Figure 5:
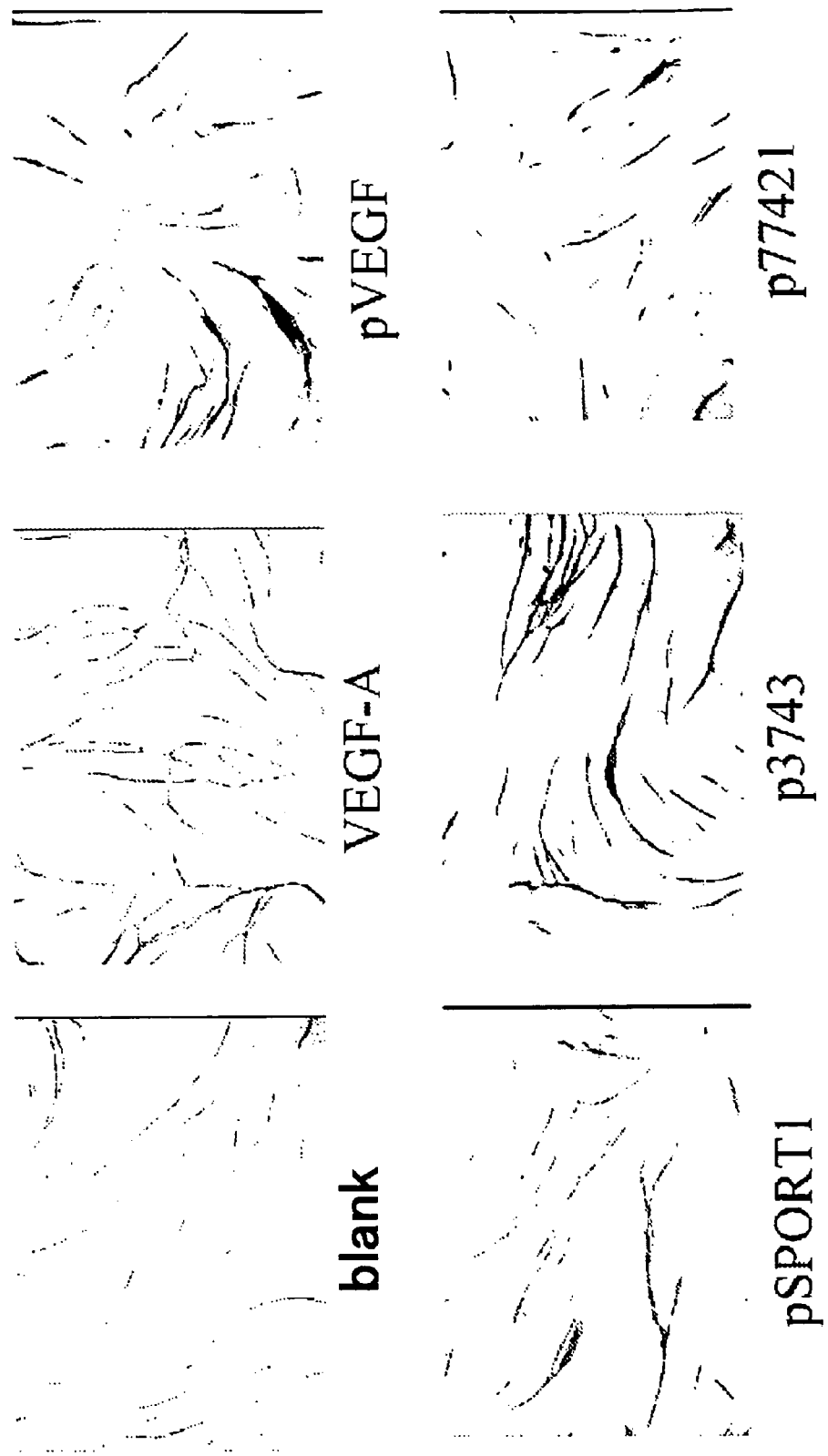
FIG. 5 is a photograph showing the results of angiogenesis activity measurement.
Figure 1:
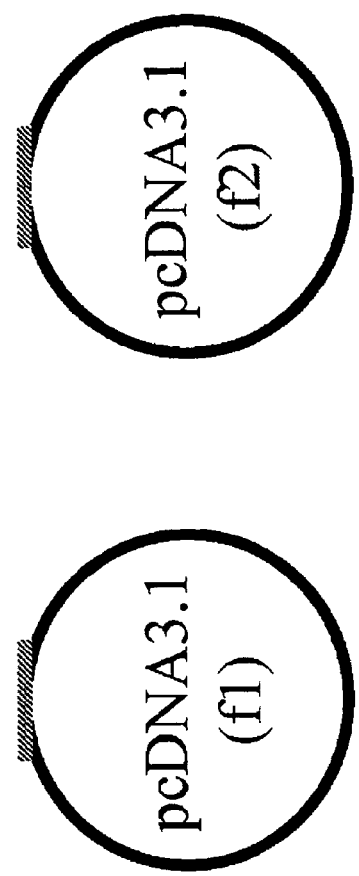

Each well was observed under a 40× magnification microscope and a photograph of each well was taken. An enlarged photograph with the scale of 1 mm magnified 40-fold was taken (FIG. 5). When a supernatant of HAEC into which the gene had been introduced was used, tube formation occurred, as shown in FIG. 5. p77421 is one gene from a heart gene library having no proliferation activity.

Each of the resulting images was quantified with angiogenesis quantification software (KSW-5000U, Kurabo Industries Ltd.) according to the following method. The area (left in FIG. 6) and length (right in FIG. 6) of tubes formed in each visual field were measured on the scale by computer analysis with various indicators. As a result, both the area and length of the formed tubes were significantly greater with p3743, as shown in FIG. 6.

(2. Sequencing)

When sequencing was carried out, the sequence was found to be a polypeptide fragment (nucleotide sequence No. 2364-3958 in SART-2; SEQ ID NO:3) consisting of C-terminal 221 amino acids of SART-2 (nucleotide sequence No. 1-3958), reported as a cancer antigen gene. In this nucleotide sequence, there were two candidates capable of encoding the protein, that is, f1 (nucleotide sequence No. 2764-3073 (=SEQ ID NO:4) in the frame of SART-2, and F2 (nucleotide sequence No. 2660-2750) (=SEQ ID NO:1) shifted from the frame of SART-2, and thus each of these gene fragments was amplified by PCR and then ligated with an expression vector pCDNA3.1 having CMV promoter (FIG. 7). When the cell proliferation ability of each of the genes was examined by c-fos promoter assay, f1 had no activity, while F2 had the same activity as that of VEGF (FIG. 8). HGF and VEGF had almost the same activation ability in the c-fos promoter assay. Accordingly, F2 peptide was further analyzed below.

Example 4

Functional Analysis of F2 Peptide (1. Analysis, by MTS Assay, of the Ability to Proliferate HEAC Cells)

F2 peptide was synthesized and then contacted in a varying amount with HAEC, and the ability thereof to proliferate the cells was examined by MTS assay. The MTS assay is a modification of the MTT assay, and is a method of measuring living cells based on a reaction of reducing tetrazolium salt (MTS) by living cells in culture, into a colored product formazan. Specifically, this assay is carried out as follows:

HAEC was inoculated onto a 96-well plate at a density of 750 cells/well.

2 µl/well of each sample was added to 100 µl/well endothelial cell medium (1% FBS, without EGF). 2 µl/well was added every day (until Day 6) (the medium was not exchanged).

20 µl measurement solution (Cell Titer 96 AQueous One Solution Cell Proliferation Assay (Promega)) was added to each well and mixed with 100 µl of the endothelial cell medium, and the old medium was removed by suction. A mixed suspension of the measurement solution and the cells was put in a volume of 120 µl/well and then incubated for 1 to 5 hours in a $CO_2$ incubator.

The absorbance at 490 nm was measured with a plate reader.

The sample group (8 wells each) is as follows:

NC: Only EBM medium (endothelial cell medium) containing 1% FBS. The other samples were cultured by adding various peptides to this medium containing serum.

VEGF-A: Recombinant VEGF-A (KURABO) was added at a final concentration of 10 ng/ml.

F2-1: F2 peptide was added at a final concentration of 1 ng/ml.

F2-10: F2 peptide was added at a final concentration of 10 ng/ml.

F2-100: F2 peptide was added at a final concentration of 100 ng/ml.

F2-1000: F2 peptide was added at a final concentration of 1000 ng/ml.

Figure 9:
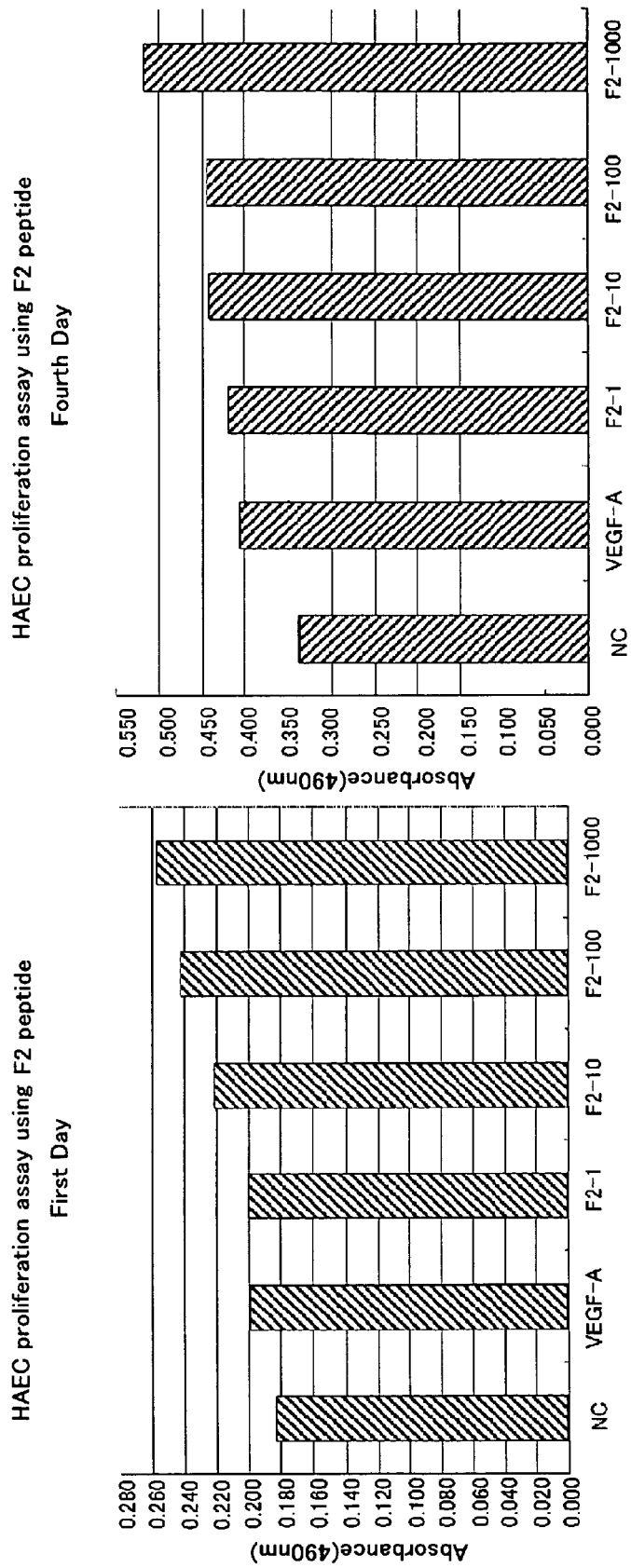
FIG. 9 shows the effects of F2 peptide on the growth of human aortic vascular endothelial cells (MTS assay).

As a result, the cell proliferation ability of F2 peptide was recognized in a dose-dependent manner, similar to VEGF protein, as shown in FIG. 9. This result indicates that F2 peptide has a stronger activity of enhancing proliferation of HEAC than VEGF. It was revealed that the amino acid sequence of F2 peptide, which is a positively charged helix peptide consisting of 30 amino acids MLSLIFLHRLKSM-RKRLDRKLRFWHRKNYP (SEQ ID NO:2), is an artificial active peptide which does not naturally occur. This peptide is a novel substance not reported with regard to either its structure or its activity.

(2. Influence of F2 Peptide on the Migration of Endothelial Cell HEAC)

The migration of HEAC endothelial cells was assayed using a modified Boyden chamber (Rikitake, Y et al., Arterioscler Thromb Vasc Biol 20, 1006-1012 (2000)). A polyvinyl pyrrolidone (PVP)-free polycarbonate membrane having 8-µl pores (Neuro Probe Inc., Gaithersburg, Md.) was coated overnight with 0.1% gelatin and then washed with phosphate buffered saline to remove an excess of the gelatin coating. Then, 28 µl growth factor-free EBM2 medium supplemented with 1% FBS was arranged in a lower chamber, and the membrane was arranged on the lower chamber. Then, the cells were suspended at $1 \times 10^6$ cells/ml in 50 µl EBM2 medium containing VEGF-A (50 ng/ml, Kurabo, Osaka, JP) or F2 peptide (10 ng/ml, 100 ng/ml, 1 µg/ml), or a control peptide (1 µg/ml; amino acid sequence RSLEGTDRFPFVR-LKNSRKLEFKDIKGIKR, SEQ ID NO:6). The Boyden chamber was incubated at 37° C. for 4 hours. After incubation, the membrane was removed and the cells on the upper side of the membrane were removed. The cells on the lower side of the membrane were stained with Diff-Quick (Sysmex, Hyogo Pref., JP). The cells in each of randomly selected 8 visual fields (×100) were counted.

Figure 10:
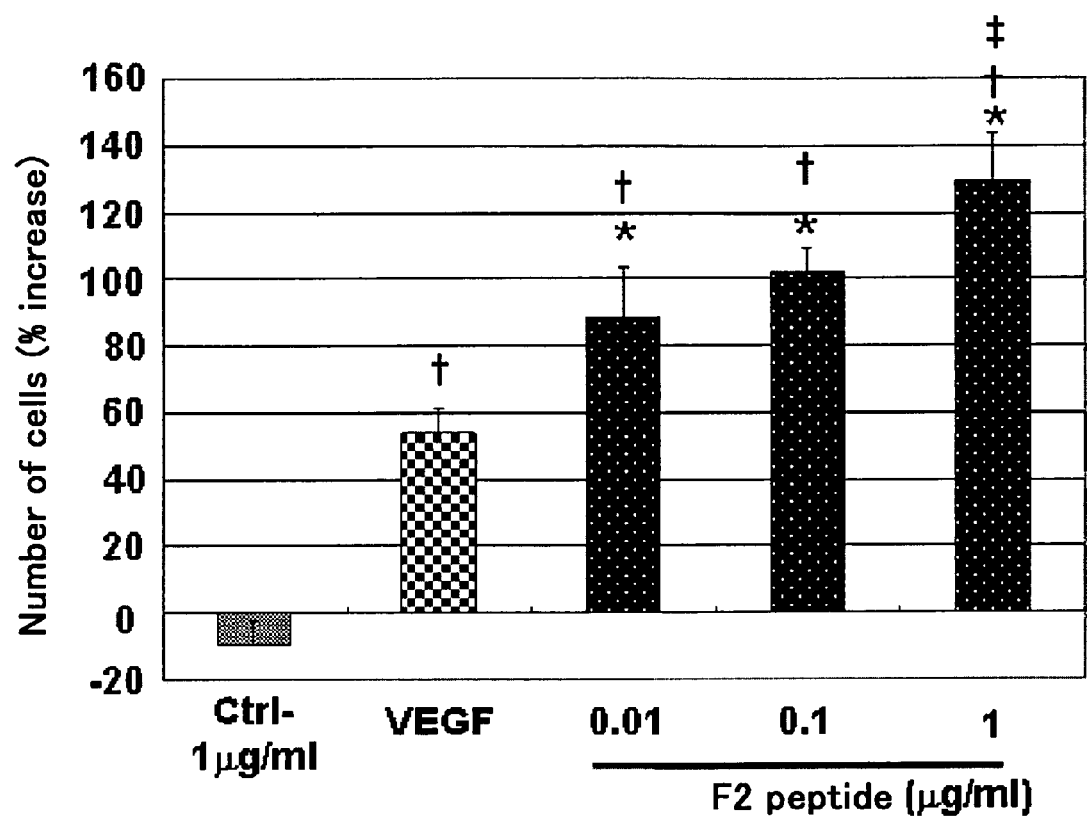
FIG. 10 shows the effects of F2 peptide at varying concentrations on the growth of endothelial cells.
Figure 11:
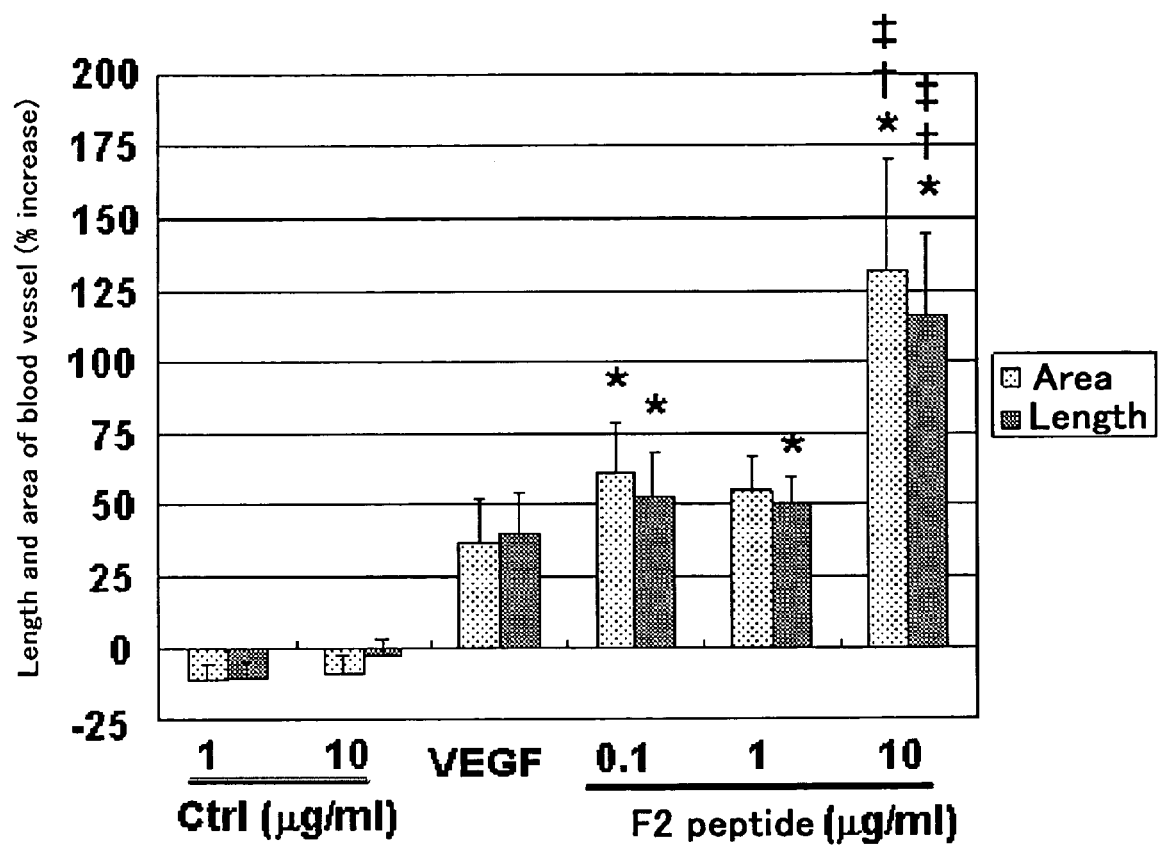
FIG. 11 shows the effects of F2 peptide at varying concentrations on the growth of endothelial cells. The results of a control peptide and VEGF as comparative controls are also shown.

When the HEAC endothelial cells were treated with F2 peptide, cell migration activity was significantly increased in a concentration-dependent manner (0.01 to 1 µg/ml). The results are shown in FIG. 10 and Table 1 below.

TABLE 1

|  | Control 1 µg/ml | VEGF 50 ng/ml | F2 10 ng/ml | F2 100 ng/ml | F2 1 µg/ml |
|---|---|---|---|---|---|
| % Increase | −10.1 | 53.8 | 88.5 | 102.5 | 129.8 |
| Standard error | 7.472 | 7.505 | 15.11 | 7.038 | 13.794 |

The migration of the endothelial cells was not observed with 1 µg/ml control peptide (expressed as Ctrl). The effect of F2 peptide on the migration of endothelial cells was higher than that of VEGF (50 ng/ml). This result indicates that F2 peptide has a higher activity in promoting migration of HEAC cells than that of VEGF.

(3. Confirmation of the In Vitro Angiogenesis Activity of F2 Peptide)

By examining in vitro promotion of angiogenesis by treatment with F2 peptide, the angiogenesis activity of F2 peptide was confirmed. According to the method described in "1. Angiogenesis activity" in Example 3, VEGF-A (50 ng/ml), F2 peptide (0.1, 1, 10 µg/ml) and the control peptide (1, 10 µg/ml) were examined for their vascularization activity.

It was confirmed that larger blood vessels were formed by treatment with F2 peptide than by treatment with recombinant VEGF (50 ng/ml) or the control peptide. The results are shown in FIG. 1 and Table 2 below.

TABLE 2

|  |  | Control 1 μg/ml | Control 10 μg/ml | VEGF-A 50 ng/ml | F2 100 ng/ml | F2 1 μg/ml | F2 10 μg/ml |
|---|---|---|---|---|---|---|---|
| % Increase | Area | −12 | −9 | 37 | 61 | 55 | 132 |
|  | Length | −11 | −3 | 40 | 53 | 50 | 116 |
| Standard error | Area | 6 | 6 | 15 | 18 | 12 | 38 |
|  | Length | 6 | 6 | 14 | 15 | 10 | 28 |

This result indicates that F2 peptide has a stronger angiogenesis enhancing activity than that of VEGF.

(4. Confirmation of the In Vivo Angiogenesis Activity of F2 Peptide)

In order to examine the in vivo angiogenesis-promoting activity of F2 peptide, a Matrigel plug assay (Rikitake, Y et al., Arterioscler Thromb Vasc Biol 20, 1006-1012 (2000)) was carried out. Together with any one of VEGF-A (50 ng/ml), F2 peptide (1 μg/ml) or the control peptide (1 μg/ml) or without adding any sample (negative control), Matrigel (0.5 ml, BD Biosciences, Franklin Lakes, N.J.) depleted of growth factor was mixed with 40 U/ml heparin (Aventis Pharma, Tokyo, JP). Then, each mixture was injected subcutaneously into a C57BL/6 female mouse obtained from Oriental Bioscience (Kyoto, JP). After 7 days, the mouse was sacrificed, and the plug was recovered and fixed in methanol. For immune staining, the section was incubated overnight at 4° C. with anti-CD31 (PECAM-1) monoclonal antibody (diluted at 1:100, BD Pharmigen, San Diego, Calif.) and then incubated for 2 hours with Alexa Flour 488 secondary antibody (1:1000, Molecular Probes, Eugene, Oreg.) before photographing. Every experimental protocol was approved by Animal Committee, Medical Department, Graduate School, Osaka University, JP.

The mouse receiving the F2 peptide-containing Matrigel indicated more newly formed blood vessels containing intact erythrocytes than in the mouse receiving a Matrigel containing the control peptide. The results are shown in FIG. 12 (×100).

By immune staining with anti-CD31 antibody, it was confirmed that more newly formed blood vessels occurred in the group treated with F2 than in the group not treated with F2. The results are shown in FIG. 13 (×100). The above demonstrated results and these data indicated that F2 peptide increases the migration of endothelial cells and induces the invasion of endothelial cells into the F2 peptide-containing gel.

Example 5

Figure 14:
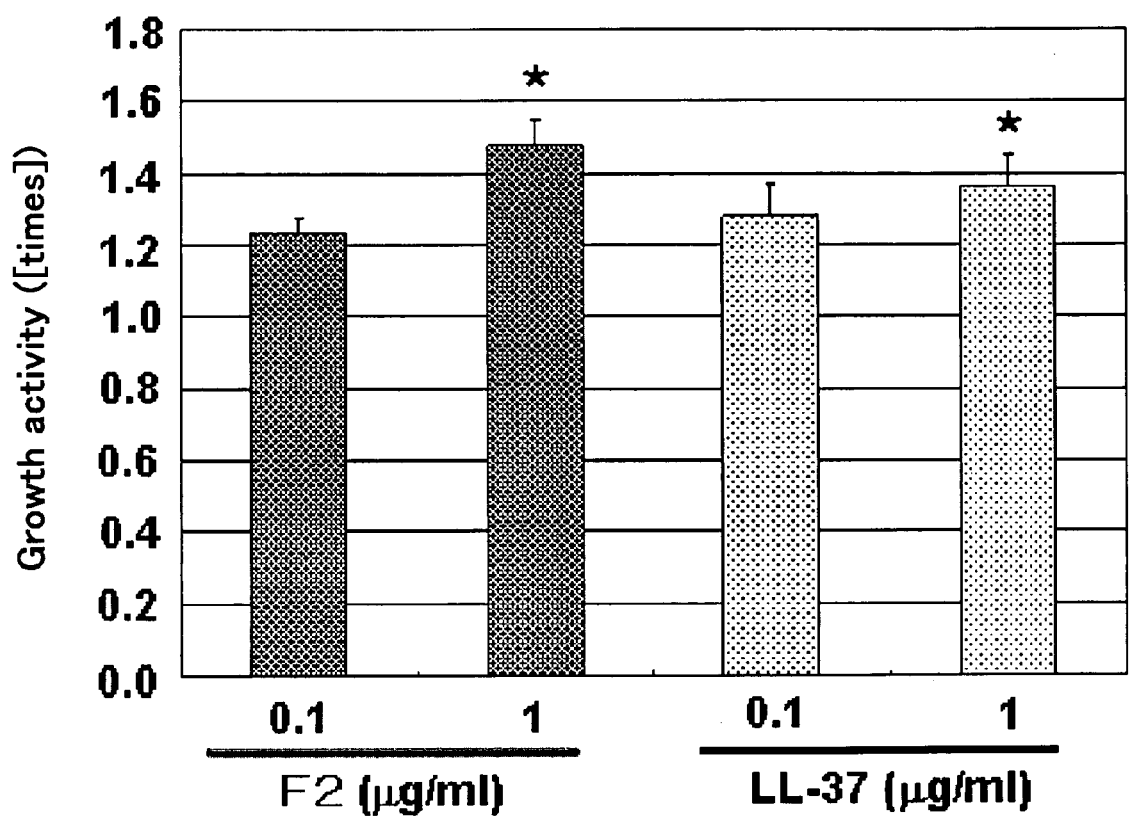
FIG. 14 shows the effects of F2 peptide at varying concentrations and LL-37 peptide at varying concentrations on the growth of endothelial cells.

Comparison Between Peptide LL-37 Having an Antimicrobial Activity, an Angiogenesis Activity and an Artery-Forming Activity, and F2 Peptide A protein homologous in structure with F2 peptide could not be found by database search. As a result of structural analysis, F2 peptide forms an α-helix structure and is thus suggested to interact with a membrane and to have antimicrobial activity. LL-37 peptide is known to be a peptide having antimicrobial activity, angiogenesis activity and artery-forming activity. Actually LL-37 peptide is similar to F2 peptide in that it is rich in arginine and forms an α-helix structure. Accordingly, the effect of LL-37 was compared with the effect of F2 peptide. As a result, both the peptides showed their activity at similar degrees in the endothelial proliferation assay using MTS. The results are shown in FIG. 14 and Table 3 below.

TABLE 3

|  | F2 100 ng/ml | F2 1 μg/ml | LL37 100 ng/ml | LL37 1 μg/ml |
|---|---|---|---|---|
| Increase [times] | 1.23 | 1.475 | 1.279 | 1.361 |
| Standard error | 0.04 | 0.07 | 0.09 | 0.09 |

Figure 15:
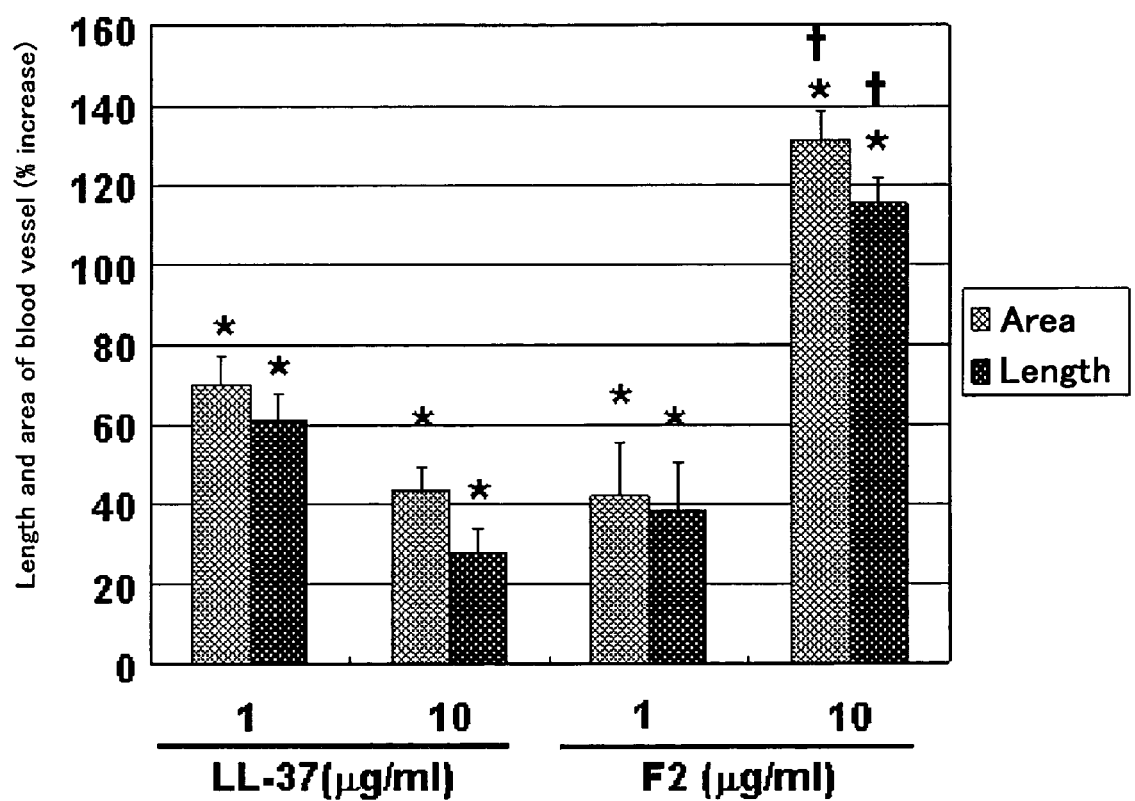
FIG. 15 shows the results of the angiogenesis promotion activities of F2 peptide at varying concentrations and LL-37 peptide at varying concentrations.

However, F2 peptide showed higher angiogenesis activity at a dose of 10 μg/ml than that of LL-37 peptide. This result is shown in FIG. 15 and Tables 4 and 5 below.

TABLE 4

|  | LL37 1 μg/ml | LL37 10 μg/ml | F2-1 1 μg/ml | F2-10 10 μg/ml |
|---|---|---|---|---|
| Area (% increase) | 70.1 | 43 | 41.8 | 131.4 |
| Standard error | 7.1 | 6.1 | 13.6 | 6.9 |

TABLE 5

|  | LL37 1 μg/ml | LL37 10 μg/ml | F2-1 1 μg/ml | F2-10 10 μg/ml |
|---|---|---|---|---|
| Length (% increase) | 60.9 | 28 | 38.5 | 115.5 |
| Standard error | 6.9 | 6 | 12.1 | 6 |

Figure 16:
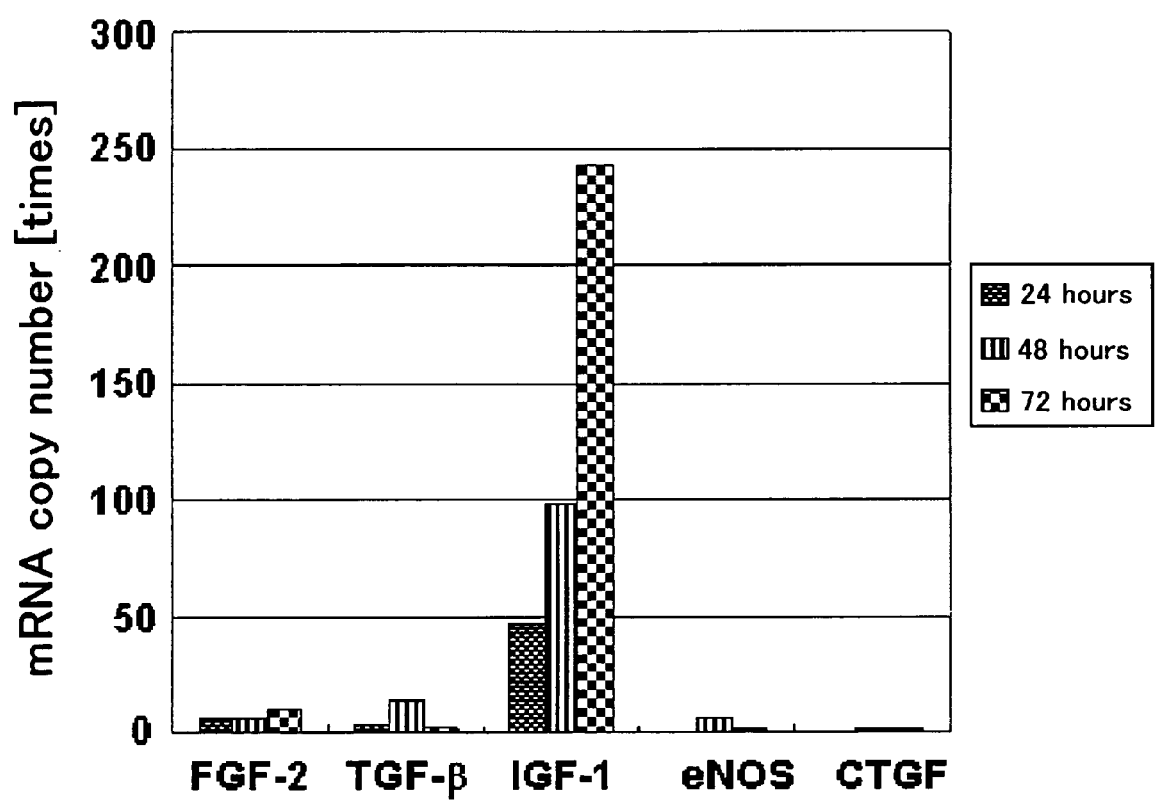
FIG. 16 shows the effects of F2 peptide on the expression levels of mRNAs encoding various growth factors.

According to a previous study, it is known that ERK (extracellular signal-related kinase) and phosphatidyl inositol-3-kinase/Akt (PI3K/Akt) activity is increased rapidly by LL-37. F2 peptide, on the other hand, did not have any direct effect on ERK activity or PI3K/Akt activity (data are not shown) As shown in FIG. 16 and Table 6 below, however, F2 peptide up-regulated the mRNA level of insulin-like growth factor-1 (IGF-1) potently and specifically in a time-dependent manner over 72 hours.

TABLE 6

|  | FGF-2 | TGF-b | IGF-1 | eNOS | CTGF |
|---|---|---|---|---|---|
| 24 hrs | 5.7 | 2.6 | 46.2 | 0.1 | 0.2 |
| 48 hrs | 6.0 | 13.6 | 97.9 | 6.1 | 1.1 |
| 72 hrs | 9.4 | 1.6 | 243.8 | 0.7 | 0.5 |

(3) Increased Amount [times]

On the other hand, F2 peptide did not have any effect on the mRNA levels of fibroblast growth factor (FGF-2), transforming growth factor (TGF-β), endothelial nitric oxide synthase (eNOS) or connective tissue growth factor (CTGF). The increase in IGF-1 expression induced by F2 peptide is important. This is because IGF-1 acts as a growth factor having an angiogenesis activity and having a broad spectrum involved in vascular reconstruction. Further, IGF-1 stimulates hypoxia inducible factor-α and its downstream effecter VEGF, thereby promoting angiogenesis. These results indicate that F2 can induce angiogenesis by IGF-1.

The above results indicate that the effect of F2 peptide is durable. Accordingly, F2 peptide can be suitable for clinical therapy using angiogenesis. Secondary effects of F2 peptide include 1) IGF-1 mediated upregulation of VEGF expression, 2) IGF-1 mediated Akt activation and subsequent eNOS activation or anti-apoptosis effect, thereby further promoting angiogenesis. Further, IGF-1 can also stimulate muscle myogenesis and wound healing to repair tissues. Accordingly, F2 peptide is also useful in wound healing and tissue repair.

Example 6

Treatment of Diseases with the Polypeptide Encoded by the Isolated Gene Clone and with the Polynucleotide The composition of the present invention can be used to promote angiogenesis in a subject. According to Example 2, the F2 peptide expression vector is encapsulated into an HVJ envelope vector. SD rats (400 to 500 g, Charles River Japan, Inc.) were anesthetized by intraperitoneal administration of sodium pentobarbital (0.1 ml/100 mg), kept warm, and their respiration secured with an automatic respirator. The rat was subjected to left thoracotomy, and using a 30 G needle, the HVJ envelope vector (20 μl) was carefully injected directly into the apex of heart.

Test Example 1

Expression of F2 Peptide in Rat Coronary Arterial Endothelial Cells Sensitized with HVJ Envelope Vector Rat coronary arterial endothelial cells (number of cells: $10^8$) are sensitized with the HVJ envelope vector (concentration of F2 peptide expression vector in the vector: 10 μg/ml), and the amount of F2 produced is measured by ELISA method. As a control, an envelope vector not containing the F2 peptide expression vector is used and examined in the same test as described above. Separately, non-sensitized rat coronary arterial endothelial cells are measured for the amount of F2 peptide produced (untreated group). The rat coronary arterial endothelial cells sensitized with the HVJ envelope vector are confirmed to produce and secrete F2 peptide at high levels.

Test Example 2

Effect of F2 Peptide Expression Vector on Growth of Endothelial Cells

Human endothelial cells are sensitized with the HVJ envelope vector and then cultured in the presence or absence of human F2 peptide added externally (1, 10 and 100 ng/ml), to determine the increase (%) of the number of cells. It is confirmed that the growth of endothelial cells is promoted by the externally added F2 peptide. Separately, endothelial cells sensitized with the HVJ envelope vector (concentration: 10 μg/ml) are cultured and an increase in the number of cells is measured to determine percentage increase (%). It is confirmed that the percentage increase of the endothelial cells sensitized with the HVJ envelope vector is significantly higher than by the control (HJV envelope vector not containing the expression vector). Further, the endothelial cells sensitized with the HVJ envelope vector are cultured in the presence or absence of rabbit anti-human F peptide antibody, and then an increase in the number of cells is measured to determine percentage increase (%).

Test Example 3

Growth of Newly Formed Blood Vessels in the Rat Heart Muscle into Which HVJ-Liposome-DNA was Directly Injected The rat heart muscle into which the HVJ envelope vector containing the F2 peptide expression plasmid was directly injected, the rat heat muscle into which the HVJ envelope vector not containing the peptide expression plasmid was directly injected, and the untreated rat heart muscle are stained by HE staining and Azan staining, and microvessels are counted under a microscope. It is confirmed that the rat heart muscle into which the HVJ envelope vector containing the F2 peptide expression plasmid was injected has a significantly increased the number of microvessels, as compared with the rat heat muscle into which the HVJ envelope vector not containing the peptide expression plasmid was injected and the untreated rat heart muscle.

Test Example 4

Repair of Joint Cartilage by Direct Introduction of HVJ Envelope Vector into the Joint Using Kirschner wire of 1.8 mm in diameter, a lesion penetrating through the subcartilaginous bone is produced in the femur intercondylar part of 10-week-old Fisher rats. One week after the operation, the HVJ envelope vector in Example 2 is introduced directly into the joint (100 μg/knee). As a control, the HVJ envelope vector not containing the expression plasmid is administered in the same amount into the joint. 1, 3, and 4 weeks after the introduction of these genes, the rats are sacrificed and the repaired site is histologically observed. It is confirmed that 3 weeks after administration of the HVJ envelope vector containing the F2 peptide expression plasmid into the joint, cartilage-like cells recognized to synthesize proteoglycan stained with toluidine blue appear in a part of the repaired site.

Example 7

Confirmation of Antimicrobial Activity by F2 Peptide

As shown in Example 5, F2 was expected to have an antimicrobial activity from the result of its structural analysis. Hence, it is confirmed that F2 actually has an antimicrobial activity.

(Method of Evaluating Antimicrobial Activity)

The antimicrobial activity is evaluated according to US National Committee for Clinical Laboratory Standard (NCCL Documents M7-A3). That is, the minimum concentration of the peptide at which microbial growth is inhibited is determined on a microtiter plate. A microorganism is cultured for 16 hours and then the absorbance at $A_{600}$ thereof measured. From correlation of predetermined turbidity with colony forming unit (CFU), the peptide is diluted with a medium to attain a specified CFU. Each microorganism strain is added at about $5 \times 10^5$ CFU/ml (final concentration). 5 mM aqueous solution of each peptide and 1.6 mM solution using a medium are prepared and used in serial dilution. 50 µl peptide at each concentration is pipetted into each well of a microtiter plate into which 50 µl/well microbial suspension has been pipetted (the final concentration of the peptide is 3.1 µM to 800 µM). A well to which the peptide was not added is used as the negative control. The plate is subjected to stationary culture at 37° C. for 18 hours and the minimum concentration at which microbial growth is inhibited (minimum inhibitory concentration (MIC)) is determined. The concentration shown as results is MIC (µM). According to this method, the antimicrobial activity of the F2 peptide is determined.

The present invention has been illustrated by reference to preferable embodiments of the invention, but it should not be construed that the present invention is limited to such embodiments. It is construed that the scope of the invention should be defined only by the appended claims. It should be construed that from the description of specific preferred embodiments of the invention, those skilled in the art can carry out the equivalent scope on the basis of the description of the invention and technical common knowledge. It is construed that the disclosure of the patents, patent applications and literatures cited in this specification should be incorporated herein by reference in their entirety to the same extent as if the disclosure of each had been included verbatim in the specification.

INDUSTRIAL APPLICABILITY

By isolating a novel peptide having angiogenesis activity and a gene encoding the peptide, there is provided a novel pharmaceutical composition for treatment, prevention, and prognosis of a disease selected from the group consisting of arteriosclerosis obliterans, Buerger disease, peripheral blood vessel disease, angina, myocardial infarction, cerebral infarction, ischemic heart disease, and ischemic cerebral disease. There is also provided an antimicrobial composition comprising the peptide of the invention.

The invention claimed is:

1. An isolated polypeptide encoded by the polynucleotide sequence consisting of SEQ ID NO:1.

2. A pharmaceutical composition for growth of vascular endothelial cells, which comprises the polypeptide of claim 1.

3. A pharmaceutical composition for the treatment of a disease selected from the group consisting of occlusive arterial disease, arteriosclerosis obliterans, Buerger disease, angina, myocardial infarction, cerebral infarction, ischemic heart disease, and ischemic cerebral disease, which comprises the polypeptide of claim 1.

4. An isolated polypeptide consisting of the amino acid sequence of SEQ ID NO:2.

5. The isolated polypeptide according to claim 4, which has angiogenesis activity.

6. The isolated polypeptide according to claim 4, which has vascular endothelial cell growth activity.

7. A pharmaceutical composition for angiogenesis, which comprises the polypeptide of claim 4.

8. A pharmaceutical composition for growth of vascular endothelial cells, which comprises the polypeptide of claim 4.

9. A pharmaceutical composition for the treatment of a disease selected from the group consisting of occlusive arterial disease, arteriosclerosis obliterans, Buerger disease, angina, myocardial infarction, cerebral infarction, isehemic heart disease, and ischemic cerebral disease, which comprises the polypeptide of claim 4.

* * * * *

UNITED STATES PATENT AND TRADEMARK OFFICE
CERTIFICATE OF CORRECTION

PATENT NO. : 7,807,176 B2
APPLICATION NO. : 10/593518
DATED : October 5, 2010
INVENTOR(S) : Tomoyuki Nishikawa et al.

It is certified that error appears in the above-identified patent and that said Letters Patent is hereby corrected as shown below:

Column 52, line 57, claim 9, the phrase "angina, myocardial infarction, cerebral infarction, isehemic" should read -- angina, myocardial infarction, cerebral infarction, ischemic --.

Signed and Sealed this

Sixteenth Day of November, 2010

David J. Kappos
*Director of the United States Patent and Trademark Office*